United States Patent
Shingler et al.

(10) Patent No.: US 12,320,528 B2
(45) Date of Patent: Jun. 3, 2025

(54) AIR FLOW MANAGEMENT FOR COOKING SYSTEM

(71) Applicant: EVO AMERICA, LLC, Tualatin, OR (US)

(72) Inventors: Robert A. Shingler, Beaverton, OR (US); Joseph R. Shaw, Beaverton, OR (US)

(73) Assignee: EVO AMERICA, LLC, Tualatin, OR (US)

( * ) Notice: Subject to any disclaimer, the term of this patent is extended or adjusted under 35 U.S.C. 154(b) by 496 days.

(21) Appl. No.: 17/589,655

(22) Filed: Jan. 31, 2022

(65) Prior Publication Data

US 2022/0154944 A1    May 19, 2022

Related U.S. Application Data

(63) Continuation-in-part of application No. 16/698,826, filed on Nov. 27, 2019, now Pat. No. 11,236,913.

(51) Int. Cl.
*F24C 15/20*     (2006.01)
*A61L 9/00*      (2006.01)
(Continued)

(52) U.S. Cl.
CPC ............ *F24C 15/205* (2013.01); *A61L 9/015* (2013.01); *A61L 9/046* (2013.01); *B01D 53/38* (2013.01);
(Continued)

(58) Field of Classification Search
CPC ........ F24C 15/205; A61L 9/046; A61L 9/015; B01D 53/38; B01D 53/76
See application file for complete search history.

(56) References Cited

U.S. PATENT DOCUMENTS 3,587,555 A * 6/1971 Cerola ................ F24C 15/2042
                                                          219/400
2004/0211321 A1    10/2004 Gibson
(Continued)

FOREIGN PATENT DOCUMENTS

CN       106051881 A      10/2016
DE     102016120213 A1     4/2018
(Continued)

OTHER PUBLICATIONS

ISA Korean Intellectual Property Office, International Search Report and Written Opinion issued in PCT Application No. PCT/US2023/061595, Jun. 29, 2023, WIPO, 13 pages.
(Continued)

*Primary Examiner* — Robert A Hopkins
(74) *Attorney, Agent, or Firm* — Alleman Hall & Tuttle LLP

(57) ABSTRACT

Examples are disclosed that relate to recirculating ventilation systems for cooking appliances. One example provides a cooking appliance ventilation system, comprising a ventilation duct comprising an inlet aperture configured to receive cooking exhaust, a fan configured to pull the cooking exhaust through the inlet aperture and the ventilation duct, an ozone source configured to introduce ozone into the ventilation duct; and one more ozone mitigation components positioned within the ventilation duct downstream of the ozone source.

19 Claims, 19 Drawing Sheets

(51) Int. Cl.
  *A61L 9/015* (2006.01)
  *A61L 9/04* (2006.01)
  *B01D 53/38* (2006.01)
  *B01D 53/76* (2006.01)

(52) U.S. Cl.
  CPC .......... *B01D 53/76* (2013.01); *F24C 15/2028* (2013.01); *F24C 15/2035* (2013.01); *A61L 2209/212* (2013.01); *B01D 2258/0275* (2013.01)

(56) References Cited

U.S. PATENT DOCUMENTS

| | | |
|---|---|---|
| 2013/0008429 A1 | 1/2013 | Colburn et al. |
| 2019/0240371 A1 | 8/2019 | Benedek et al. |
| 2022/0154944 A1 | 5/2022 | Shingler et al. |

FOREIGN PATENT DOCUMENTS

| | | | |
|---|---|---|---|
| EP | 1532907 A1 | | 5/2005 |
| JP | S63202225 U | * | 12/1988 |
| JP | H05261245 A | * | 10/1993 |
| JP | 2001245794 A | | 9/2001 |
| JP | 2008221047 A | * | 9/2008 |
| KR | 1020060087209 A | | 8/2006 |
| KR | 20090043224 A | | 5/2009 |

OTHER PUBLICATIONS

European Patent Office, Extended European Search Report Issued in Application No. 20893219.4, Nov. 24, 2023, Germany, 39 pages.

* cited by examiner

AIR FLOW MANAGEMENT FOR COOKING SYSTEM

CROSS REFERENCE TO RELATED APPLICATIONS

This application is a continuation-in-part of U.S. application Ser. No. 16/698,826, filed Nov. 27, 2019, the entirety of which is hereby incorporated herein by reference.

BACKGROUND

Cooking may produce various volatile and particulate byproducts. Thus, an interior cooking installation may include a ventilation system for removing such byproducts. Many ventilation systems vent to an exterior of the cooking environment to avoid recirculating such byproducts into the cooking environment. Installing such ventilation systems may be quite expensive, as installation may involve structural modifications of a cooking facility.

SUMMARY

Examples are disclosed that relate to recirculating ventilation systems for cooking appliances. One example provides a cooking appliance ventilation system, comprising a ventilation duct comprising an inlet aperture configured to receive cooking exhaust, a fan configured to pull the cooking exhaust through the inlet aperture and the ventilation duct, an ozone source configured to introduce ozone into the ventilation duct; and one more ozone mitigation components positioned within the ventilation duct downstream of the ozone source.

Another example provides a cooking appliance ventilation system, comprising a ventilation duct comprising an inlet aperture configured to receive cooking exhaust. And an ozone reduction catalyst located within the ventilation duct, the ozone reduction catalyst comprising a plurality of catalyst units arranged in a catalyst holder, each catalyst unit occupying a portion of a cross-sectional area of the ventilation duct.

Another example provides a method of operating a cooking appliance ventilation system. The method comprises drawing cooking exhaust into a ventilation duct via a fan, introducing ozone into the ventilation duct to oxidize one or more of grease and particulate matter in the cooking exhaust, filtering the cooking exhaust, reducing ozone in the ventilation duct via an ozone reduction catalyst, and outputting exhaust from the ventilation system.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

DETAILED DESCRIPTION

Figure 1:
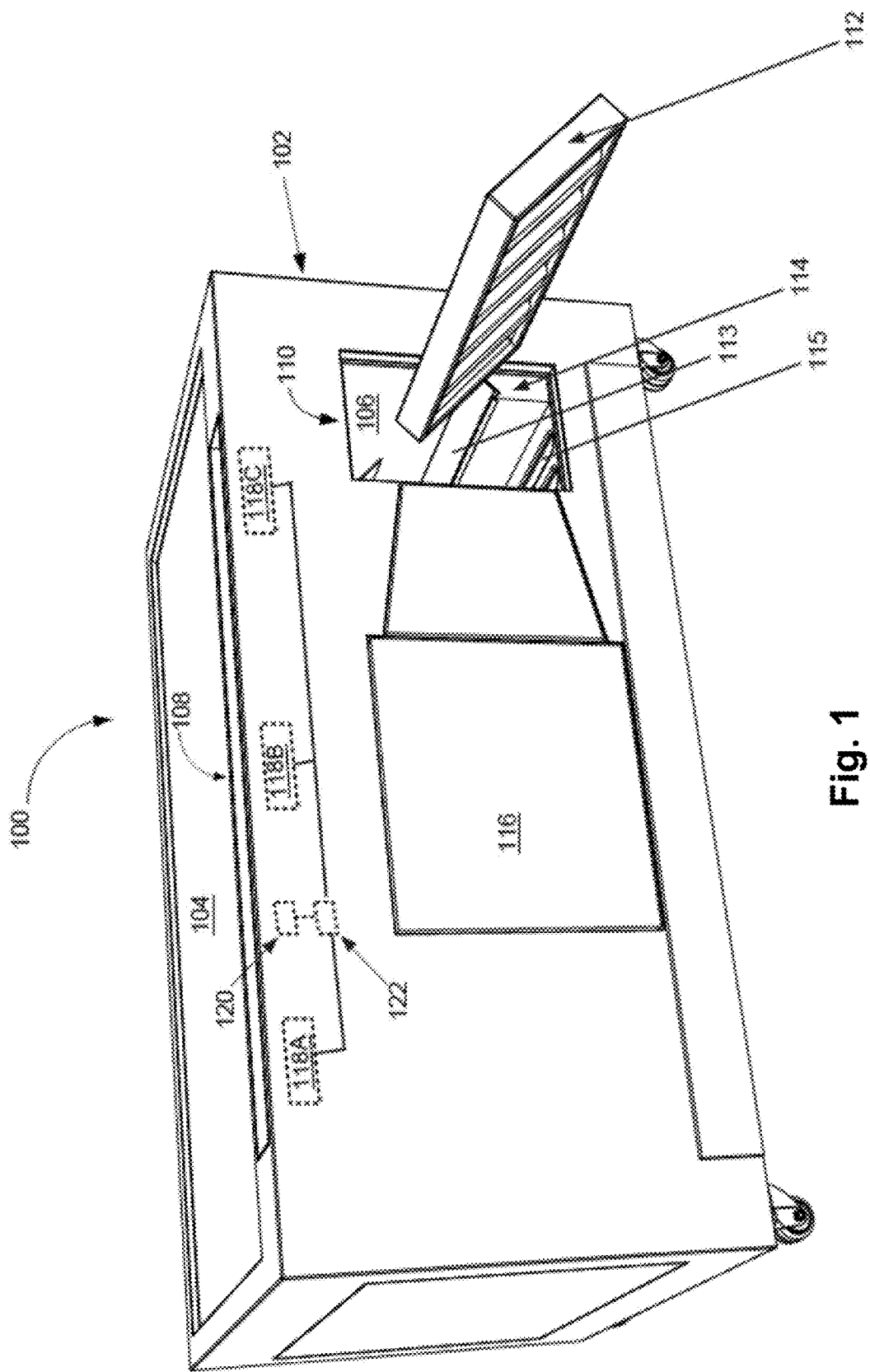
FIG. 1 shows an example cooking system, and illustrates aspects of a grease filtration stage within a ventilation duct.

In some indoor cooking settings, such as a restaurant, foods may be prepared in the presence of customers rather than in a separate kitchen. One example of such a setting is a teppanyaki-style restaurant, in which food preparation atop a large cooking surface is observed by customers sitting at a table surrounding the cooking surface. In such settings, a ventilation system hood is often positioned over the cooktop, and the ventilation system vents to the outside of the restaurant. Installing such systems may be expensive, and may involve modification of the roof and ceiling of the facility. Further, cleaning such ventilation systems may require accessing a roof of the facility.

Some indoor cooking appliances include attached ventilation systems that permit cooking exhaust to be filtered, and vented back into the occupied cooking environment. Such self-contained ventilation cooking appliance systems may be installed without modifying the roof or ceiling of the cooking environment, and thus may provide significant cost savings to a cooking facility. Such systems also may be referred to herein as recirculating ventilation systems.

However, current recirculating cooking systems may pose various issues. For example, some components, and particularly internal components, may be difficult to clean, e.g. because they are difficult to reach and/or have ventilation shapes that complicate thorough cleaning. Other components may be removable for cleaning, such as a ventilation duct inlet aperture, but still be cumbersome to clean due to having a size and/or shape incompatible with a dishwasher.

Also, relatively high-speed fans may be used in internally ventilated cooking systems to ensure that cooking exhaust is pulled into the system from across an entirety of the cooking surface to ensure capture of grease laden air and smoke, and to help cool the exhaust as it flows through the exhaust system. As the fan is located within a body of the cooking system, rather than above a ceiling or on a roof of a facility, the fan and the exhaust flow may produce an undesirable amount of noise.

Accordingly, examples of internally ventilated cooking systems are disclosed that may help to address such issues with current cooking systems with recirculating ventilation. As described in more detail below, the disclosed examples facilitate cleaning by providing various structures that improve the accessibility to internal parts that tend to gather grease and particulate deposits. These structures include removable features, such as removable support brackets for a grease filter, a removable grease collection box configured to collect grease filtered by the grease filter, a removable mount for a particulate removal system, and a multi-part removable exhaust inlet aperture, each of which may be sized to fit within a dishwashing machine in some examples. The disclosed examples also include non-removable parts that are configured to facilitate cleaning. For example, internal corners of the ventilation duct may be radiused to allow for more effective cleaning as compared to a sharply angled internal corner. The disclosed examples also may help to improve grease removal from cooking fumes, such as via of the use of an ultraviolet (UV) light treatment system, an ozone control system, a bipolar ion generator, and/or other such systems. Furthermore, the disclosed examples may include various structures to mitigate fan and exhaust noise.

FIG. 1 shows a rear perspective view of an example cooking system 100, with a grease filtration access opening in an open configuration (e.g. with a door or cover removed). The cooking system 100 includes a body 102 supporting a cooking surface 104, and a ventilation duct 106 located within the body. In this example, the ventilation duct (including associated components of a recirculating ventilation system) and a cooking appliance contained within the body, which functions as an exterior chassis, and visually appear to be a homogenous unit. In other examples, a recirculating ventilation system as described herein may be integrally attached to a cooking appliance without sharing a common body/chassis, as described in more detail with respect to FIG. 13. Continuing with FIG. 1, the ventilation duct 106 comprises an inlet aperture 108 disposed adjacent to the cooking surface 104. As described in more detail below, the cooking system 100 also comprises a removable inlet aperture (not shown in FIG. 1) extending a length of the cooking surface 104 to help direct cooking byproducts into the ventilation duct 106. The cooking system also may comprise a water spray system configured to reduce a temperature of an inlet air stream in the ventilation duct by injecting a spray of cold water into the inlet air stream. When included, the water spray system comprises nozzles 118A-118C disposed within the ventilation duct 106 and controllable to inject water into the inlet air stream to cool exhaust. In some examples, the water spray system also may include a temperature sensor 120 configured to measure inlet air temperature, and a controller 122 configured to control the spraying of water through nozzles 118A-118C, e.g. based upon a measured inlet air temperature or other suitable control input. An example water spray system is described in more detail below.

Byproducts pulled through the inlet aperture 108 and into the ventilation duct 106 enter a grease filtration stage 110 of the ventilation duct 106. The grease filtration stage 110 includes a grease filter 112 configured to separate larger grease droplets from the air flowing through the ventilation duct 106. Example filters suitable for use as the grease filter 112 include commercial grease baffle filters, such as those used in existing overhead ventilation systems.

Figure 2:
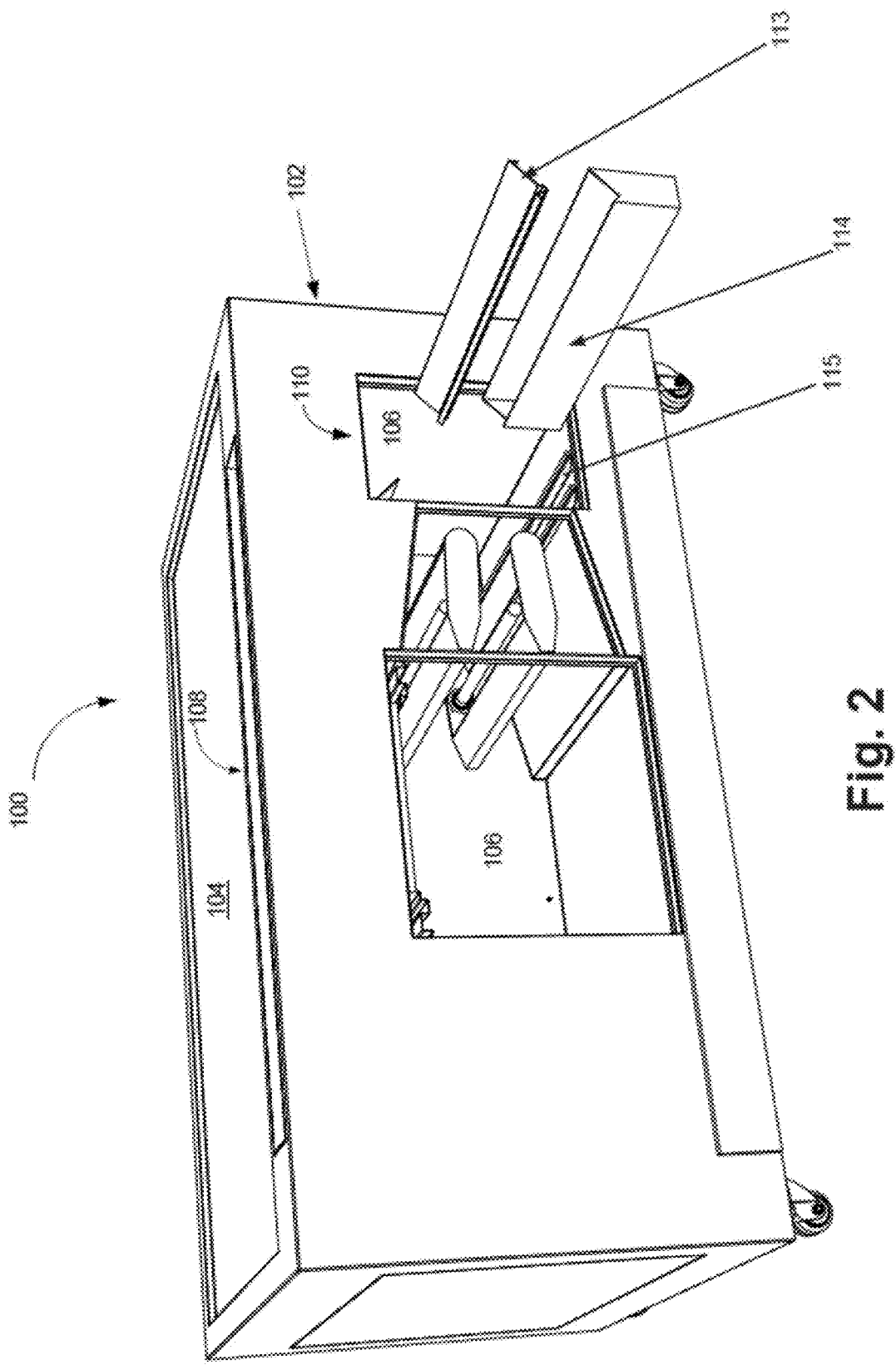
FIG. 2 shows additional aspects of the grease filtration stage of FIG. 1.

As shown in FIG. 1, the grease filter 112 is supported by a bracket 113, and is removable from the ventilation duct 106, e.g. for cleaning and/or replacement. As crevices or corners between a surface of the ventilation duct 106 and a bracket fixed (e.g. welded) to the ventilation duct may be difficult to clean by physical scrubbing, the depicted bracket 113 also is removable from the ventilation duct 106, as shown in FIG. 2, for cleaning. Further, the grease filter 112 and the bracket 113 may be sized to fit within a dishwasher, which may be more efficient and effective for cleaning than physical scrubbing.

The ventilation duct 106 further may include a grease collection box 114 configured to capture at least a portion of the grease filtered by the grease filter 112. Similar to the grease filter 112, the grease collection box 114 may also be removable from the ventilation duct 106 by a user for cleaning, as shown in FIG. 2. While referred to as a "box," the grease collection box 114 may have any suitable shape for collecting grease filtered by the grease filter. In some examples, the bracket 113 is integral with the grease collection box 114, which may help to streamline cleaning. Further, as sharp interior angled surfaces may be relatively difficult to clean, an interior of grease collection box 114 may include one or more radiused interior corners with a sufficiently wide radius of curvature to facilitate cleaning.

Figure 3:
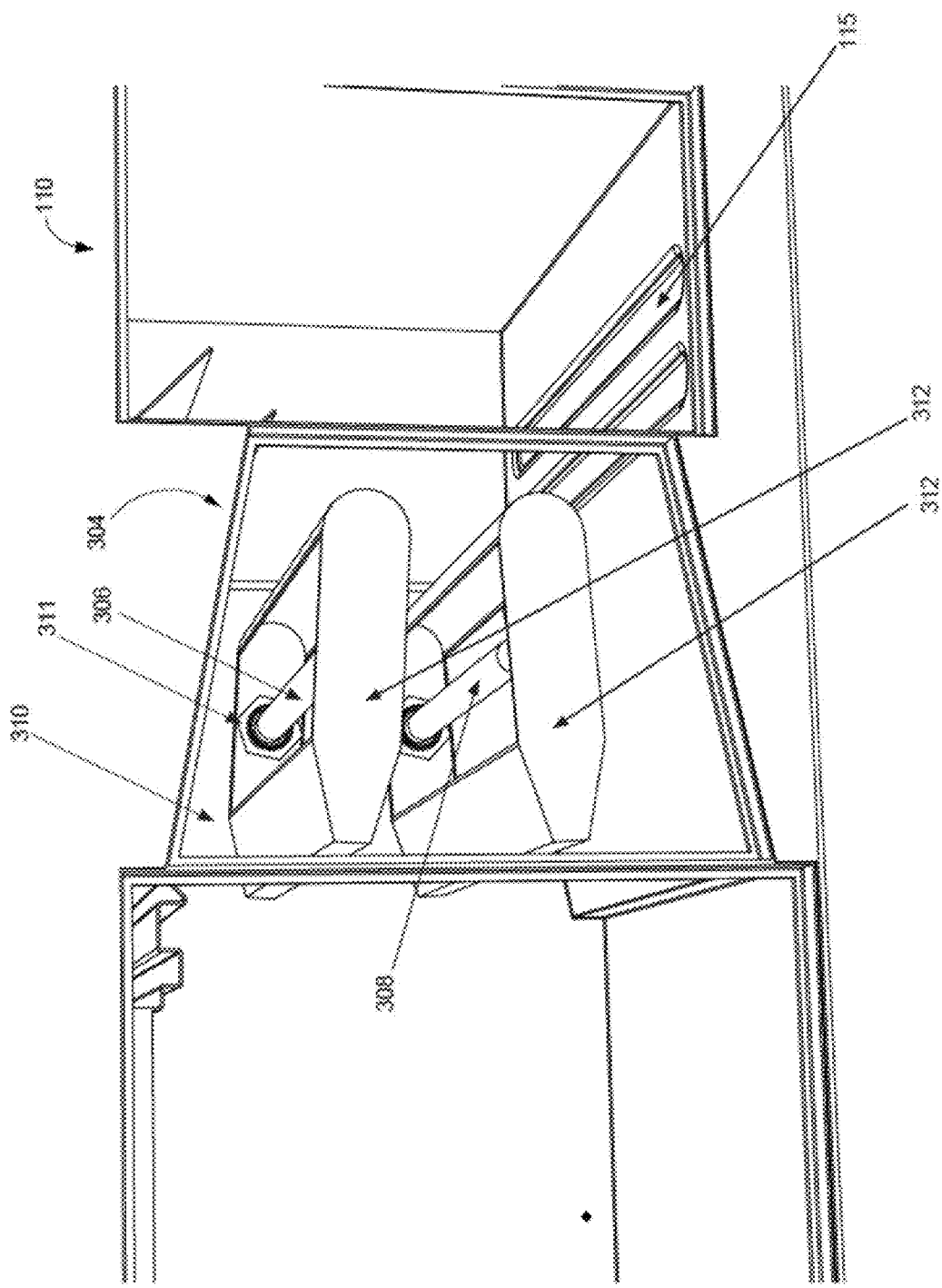
FIG. 3 shows aspects of example grease collectors and an example UV treatment stage.

The cooking system 100 also may include one or more collectors 115 within a floor of the ventilation duct 106, e.g. to collect grease filtered by the grease filter 112 that drips from the filter and is not caught by the grease collection box 114, and/or to collect grease that condenses on walls of the ventilation duct. When included, the collectors 115 may facilitate cleaning by providing a low point for condensed grease to collect. FIG. 3 shows a magnified view of the grease filtration stage 110 of FIGS. 1-2, with the grease filter and grease collection box removed. In this example, the cooking system 100 includes two elongate collectors 115 in the form of indentations within a floor of the ventilation duct 106 below the grease filter. In other examples, any other suitable number of and configuration of collectors may be used. Further, in some examples, one or more additional filters may be included downstream of the grease filter and prior to a next treatment stage of the cooking system 100. Examples of filters suitable for use include expanded aluminum or stainless-steel mesh filters, such as mist/smoke collecting MISTBUSTER filters (available from Air Quality Engineering, Inc. of Brooklyn Park, MN).

FIGS. 2 and 3 also show an ultraviolet (UV) treatment system 304 disposed within the ventilation duct downstream of the grease filtration stage 110. The UV treatment system 304 uses ultraviolet light to break down odor molecules, grease, and/or other compounds in the exhaust.

The UV treatment system 304 includes one or more first UV lamps 306 (referred hereinafter in singular form) configured to output one or more wavelengths of UV light in a wavelength range of 100 to 280 nanometers (nm). In a more specific example, the first UV lamp 306 outputs one or more wavelengths of UV light in a wavelength range of 250-260 nm. The wavelength range of the first UV lamp 306 is selected, for example, to be germicidal (UV-C) to destroy microbial moieties.

The UV treatment system 304 also includes one or more second UV lamps 308 (referred to hereinafter in singular form) configured to output UV light in a wavelength range of 160 to 240 nm. In a more specific example, the second UV lamp 308 is configured to output one or more wavelengths of UV light in a wavelength range of 180-190 nm. The wavelength range of the second UV lamp 308 is selected to generate ozone, which is an oxidant. The ozone generated by the second UV lamp 308 may react with hydrocarbons in the airflow and oxidize the hydrocarbons, thereby breaking the hydrocarbons down into smaller molecules. Some of the smaller molecules formed in this manner may precipitate from the exhaust flow as dust/soot. In some examples, one or more collectors (e.g. collectors 115) may also be positioned in a floor of the ventilation duct 106 below the UV treatment system 304 to collect such dust/soot.

The first 306 and second 308 UV lamps may be connected to a wall 310 of the ventilation duct via a socket 311 mounted to the wall 310, or in any other suitable manner. Both UV lamps may be removably mounted within the ventilation duct to allow replacement as needed.

Each UV lamp 306, 308 is shown as being positioned within an enclosure 312 that protects the UV lamp from grease and other compounds in the exhaust. This may help to prevent the formation of hotspots or other damage to the first and second UV lamps. Each enclosure 312 may be attached to the wall 310 of the ventilation duct 106 in a removable manner (e.g. via a fastener) or permanently (e.g. via welding) in various examples.

The enclosure 312 is formed at least partially from a UV-transmitting glass, quartz, or other material that is substantially transparent to the UV light from the UV lamps 306, 308. In the example shown in FIG. 3, a top surface 314 and an opposing bottom surface 316 of each enclosure 312 is formed from a UV-transparent material. Further, an interior of the ventilation duct 106 may be formed from or coated with a material that is highly UV-reflective (e.g. brushless stainless steel), which may help to reflect UV light emitted by the first 306 and second 308 UV lamps, thereby increasing a path length of the UV light and increasing a chance of interaction of the UV light with targeted molecules.

In addition to treating the flow of exhaust with ultraviolet light, the UV treatment system 304 may be configured to alter airflow characteristics. In the example shown in FIG. 3, each enclosure 312 comprises a shape and position within the UV treatment system 304 that enables the enclosure 312 to function as an air foil. This may help to increase a residence time of exhaust within the UV treatment system 304 air over the first 306 and second 308 UV lamps. In other examples, the UV filtration system 304 may include air foils attached to or separate from an enclosure 312, e.g. positioned within the ventilation duct 106 upstream of the enclosure 312. Further, in other examples, air foils of any other suitable shape may be used. In one specific example, a scallop-shaped foil (e.g. made of a UV-reflective metal) may be positioned upstream of each UV lamp (between the UV lamp and the grease filtration stage 110) to deflect the exhaust flow entering the UV treatment system 304 and thereby increase the residency time of exhaust in the UV treatment system 304.

The shape of the ventilation duct 106 within the UV treatment system 304 also may be configured to help increase the residency time of exhaust. In the depicted embodiment, the UV filtration system 304 may be disposed in a section of the ventilation duct 106 with an increasing cross-sectional area in a direction of exhaust flow. This shape allows the linear velocity of the exhaust to slow, and also may help to achieve laminar or near-laminar flow of air through the UV treatment system 304, which may produce less noise than turbulent flow. In the example shown in FIG. 3, the UV filtration system 304 is disposed within a section of the ventilation duct 106 having a trapezoidal side profile. In other examples, the ventilation duct 106 may have any other suitable cross-sectional profile.

Figure 4:
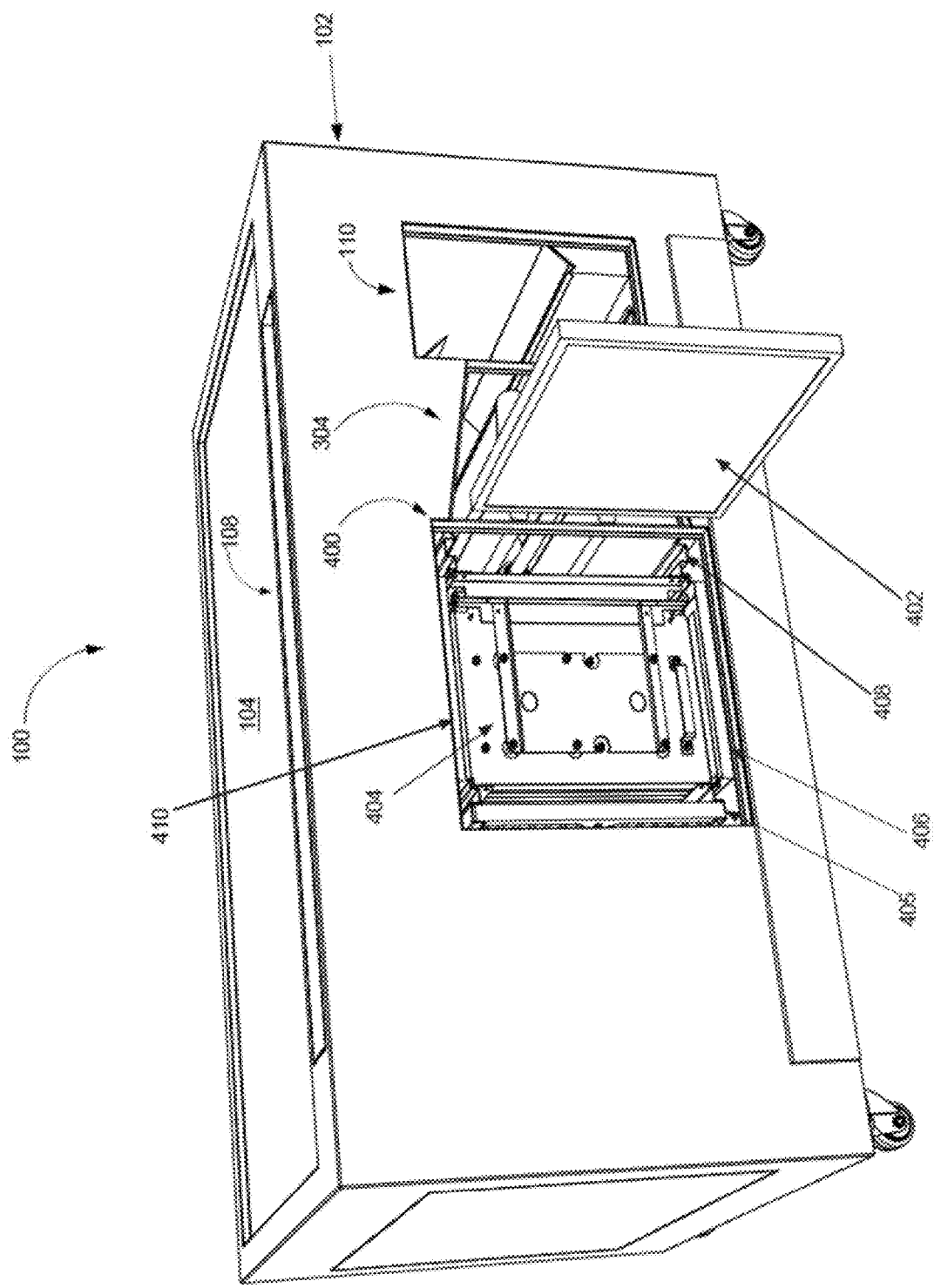
FIGS. 4-7 show aspects of an example particulate removal stage.
Figure 5:
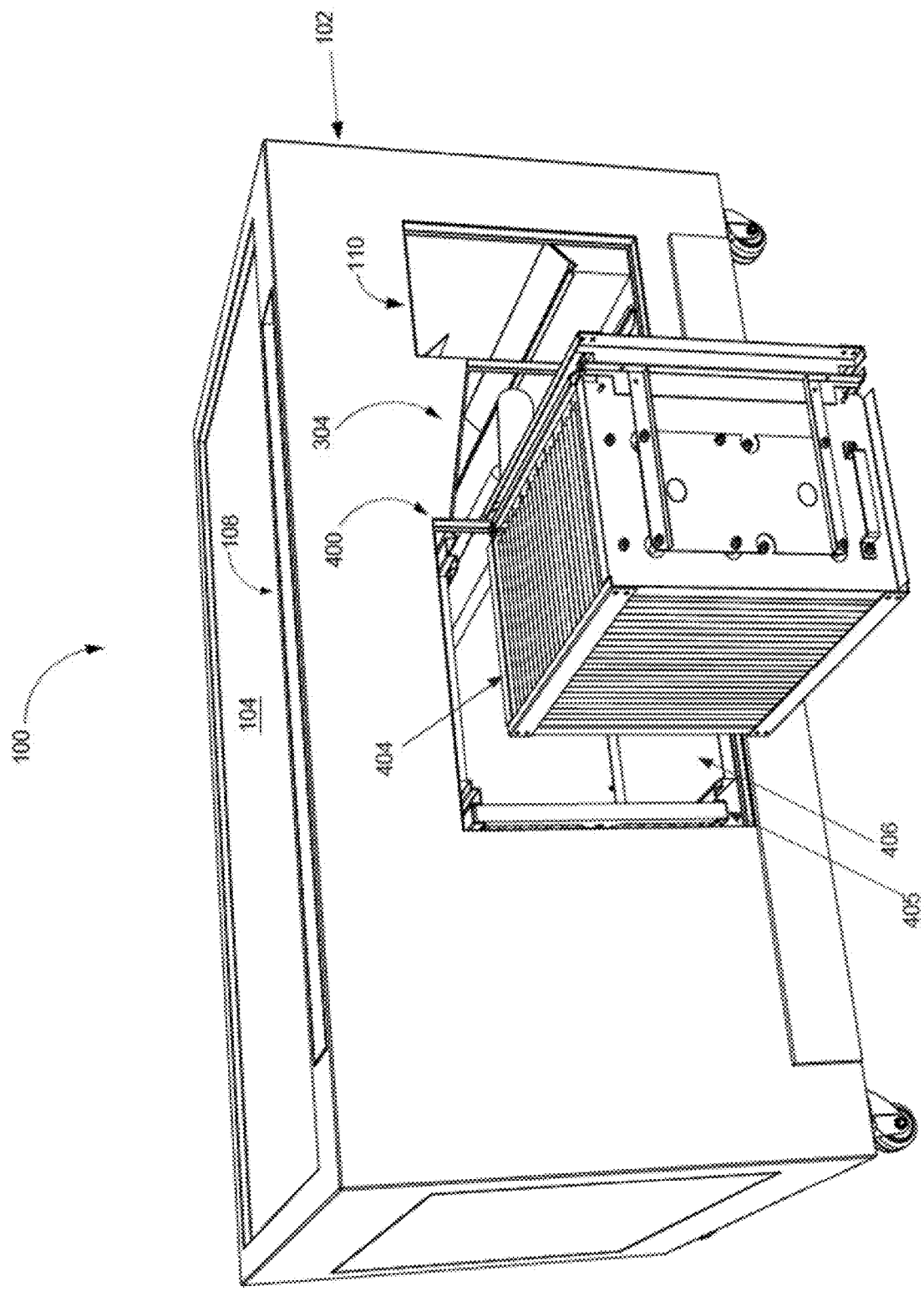
Figure 6:
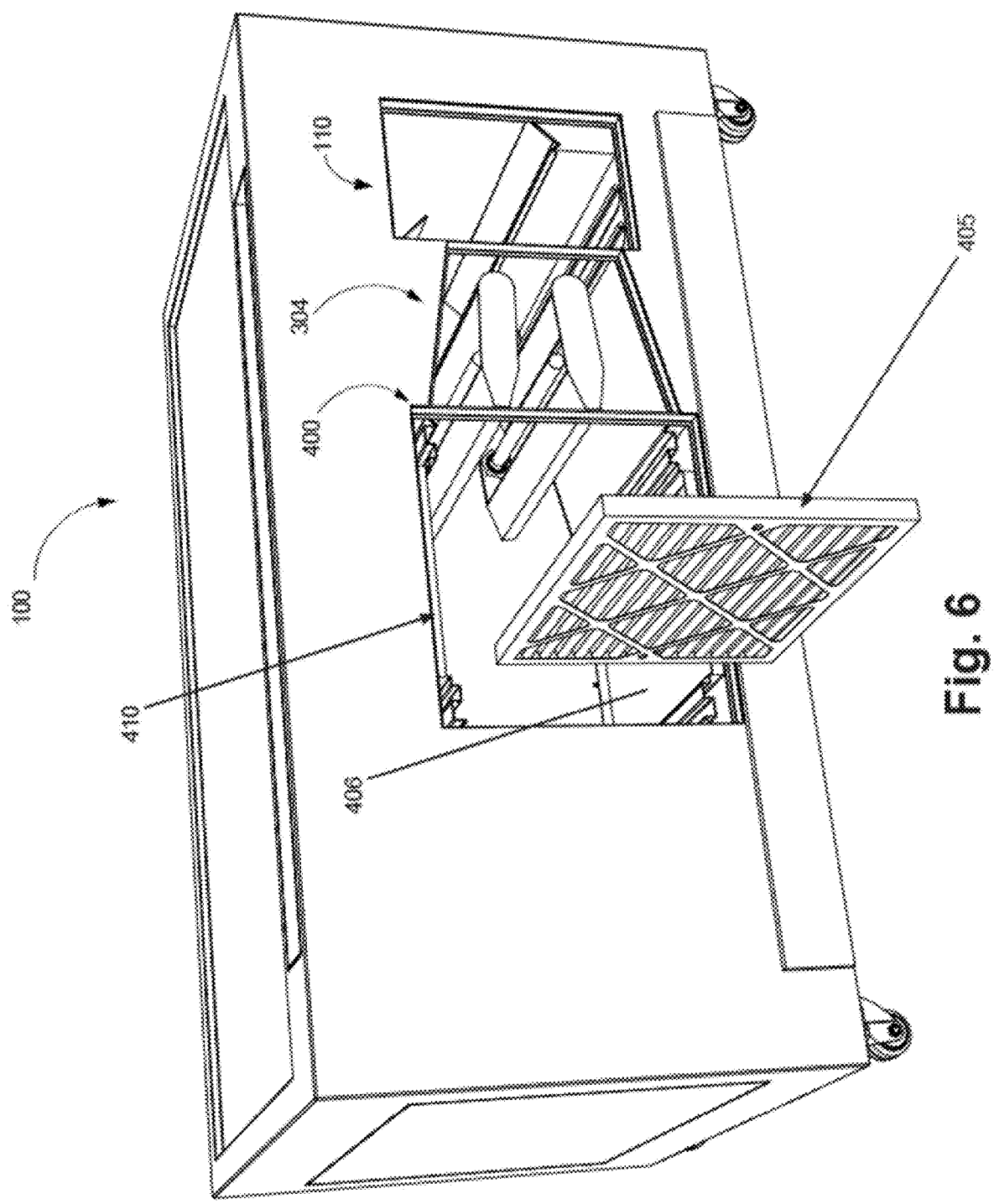

After the grease filtration stage 110 and the UV treatment system 304, the exhaust flow may still contain smaller hydrocarbons, particulate matter, and odor molecules. To further remove impurities from the air, the exhaust flow is pulled through a particulate removal system. FIG. 4 shows another rear perspective of the cooking system 100, with a particulate removal system access in an open configuration (e.g. with a door or cover removed) to illustrate an example particulate removal system 400. The depicted particulate removal system 400 includes one or more pre-filters 402 positioned upstream of an electrostatic precipitator (ESP) 404, and one or more charcoal filters 405 positioned downstream of the ESP 404. The pre-filter(s) may be configured to filter smaller droplet sizes of grease particles in the exhaust flow than the upstream filtration stages before the exhaust flow enters the ESP 404, which may help to increase precipitation efficiency of the ESP 404. Any suitable filter(s) may be used as a pre-filter 402. Examples of filters suitable for use include expanded stainless-steel or aluminum mesh filters, such as the above-mentioned MISTBUSTERS filters.

The ESP 404 includes one or more electrostatic precipitator cells configured to remove grease and other matter from the air via corona discharge. In one specific example, the ESP 404 comprises dual electrostatic precipitator cells, and at least one of the dual electrostatic precipitator cells comprises offset collection fins. The use of dual ESP cells and offset collection fins may help to filter more airborne particulates compared to a single electrostatic precipitator cell having one set of parallel collection fins.

The one or more charcoal filters 405 positioned downstream of the ESP 404 may help to further remove particulate matter, as well as volatile organic compounds (VOCs) and ozone, from the exhaust flow. As described in more detail below, the charcoal filter 405 is removable from the cooking system, e.g. for cleaning or replacement by a user. It will be noted that the use of the UV treatment system 304 upstream of the pre-filter 402 and the charcoal filter 405 may help to improve longevity of the filter(s) compared to a cooking system that omits a UV treatment system.

In existing cooking systems, an ESP and other filters (a pre-filter, a carbon filter, etc.) may be held in position within the ventilation duct via mounts, such as rails, that are welded to the interior walls of the ventilation duct. As grease and precipitated particulates may collect in the portion of the ventilation duct that holds the ESP, the grease and particulates may deposit in the corners/seams at which the ESP mounts meet the interior wall of the ventilation duct, and thus may be difficult to remove by cleaning.

Thus, the cooking system 100 includes a removeable mount for the ESP 404 and other filter(s) of the particulate removal system 400. In the depicted example, the removable mount takes the form of a grease containment pan 406 disposed beneath the ESP 404 and filters 402, 405. The filters 402, 405, the ESP 404, and the grease containment pan 406 may all be easily removed for cleaning. Further, because the ESP 404 is held in place by the grease containment pan 406, the interior surfaces of the ventilation duct in the particulate removal system 400 may be free from welded mounting structures for the ESP 404 and filters 402, 405, and thus easier to clean when the ESP 404 and filters 402, 405 are removed. The grease containment pan 406 may be held in place by the internal walls of the ventilation duct in the particular removal system 400.

Figure 7:
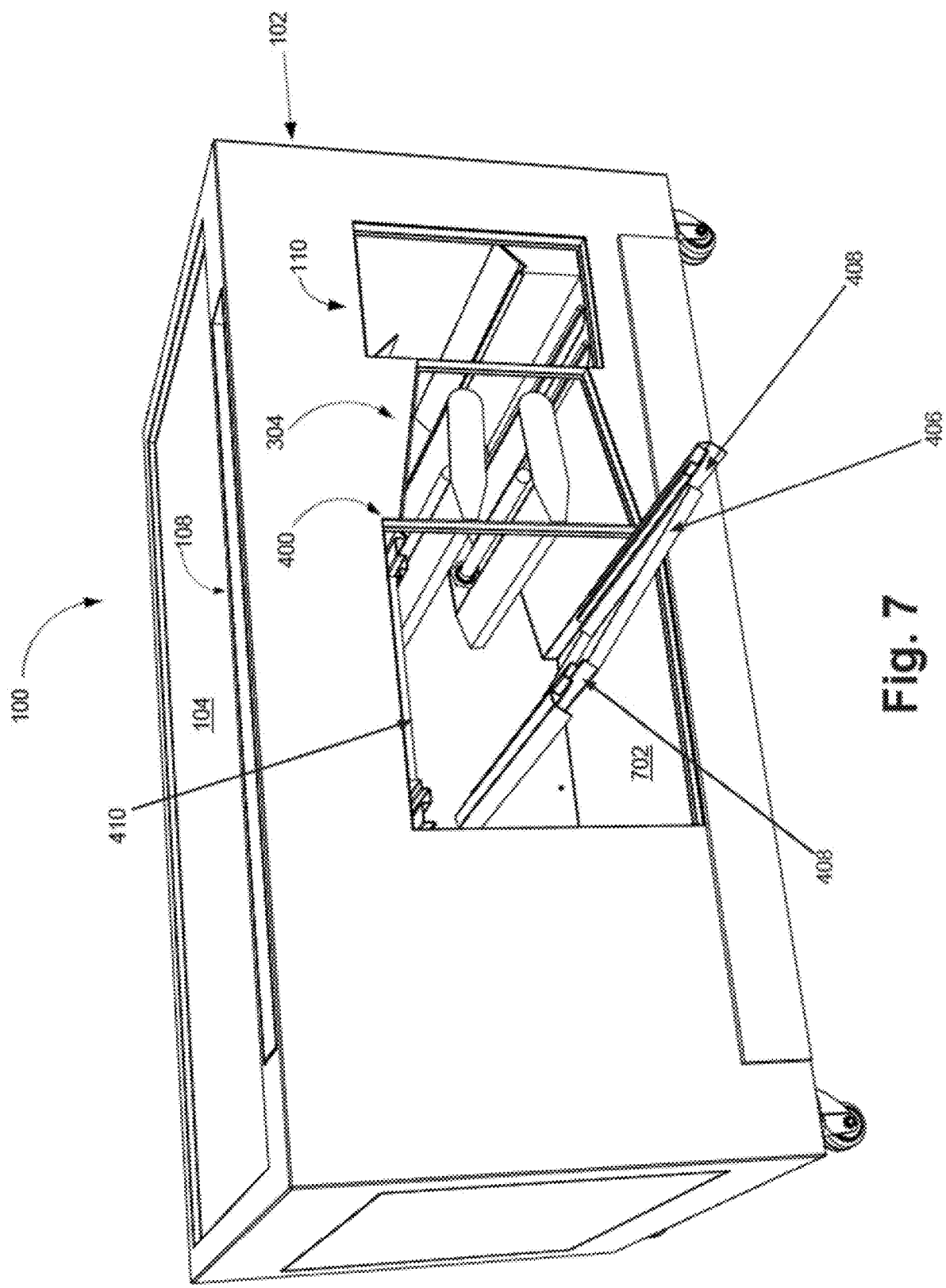

FIGS. 4-7 progressively illustrate the removal of components of the particulate removal system 400 for cleaning. First, FIGS. 4-6 respectively show the pre-filter 402, the ESP 404 and the charcoal filter 405. Then, FIG. 7 illustrates removal of the grease containment pan 406. The mounts 408 formed in the grease containment pan 406 to hold the filters 402, 405, and the ESP 404 are also shown in FIG. 7. The mounts 408 may be integral to, or affixed to, the grease containment pan 406, such that the grease containment pan 406 and mounts 408 may be removed as one piece. Once removed by a user, the grease containment pan 406 may be washed via a dishwasher.

In some examples, a cooking system may also include a top bracket 410 configured to position the particulate removal system 400 within the ventilation duct. When included, the top bracket 410 may be formed within a ceiling of the ventilation duct, such that grease may not penetrate an inaccessible surface of the ventilation duct.

In some examples, a particulate removal stage may include two or more separate, serviceable high efficiency particulate air (HEPA) filter components rather than an ESP or a one-piece HEPA filter. As different filter components may require servicing at different time intervals, the use of separate, serviceable HEPA filter components may permit servicing of individual filter components rather than servicing of an entire one-piece HEPA filter unit.

Figure 14:
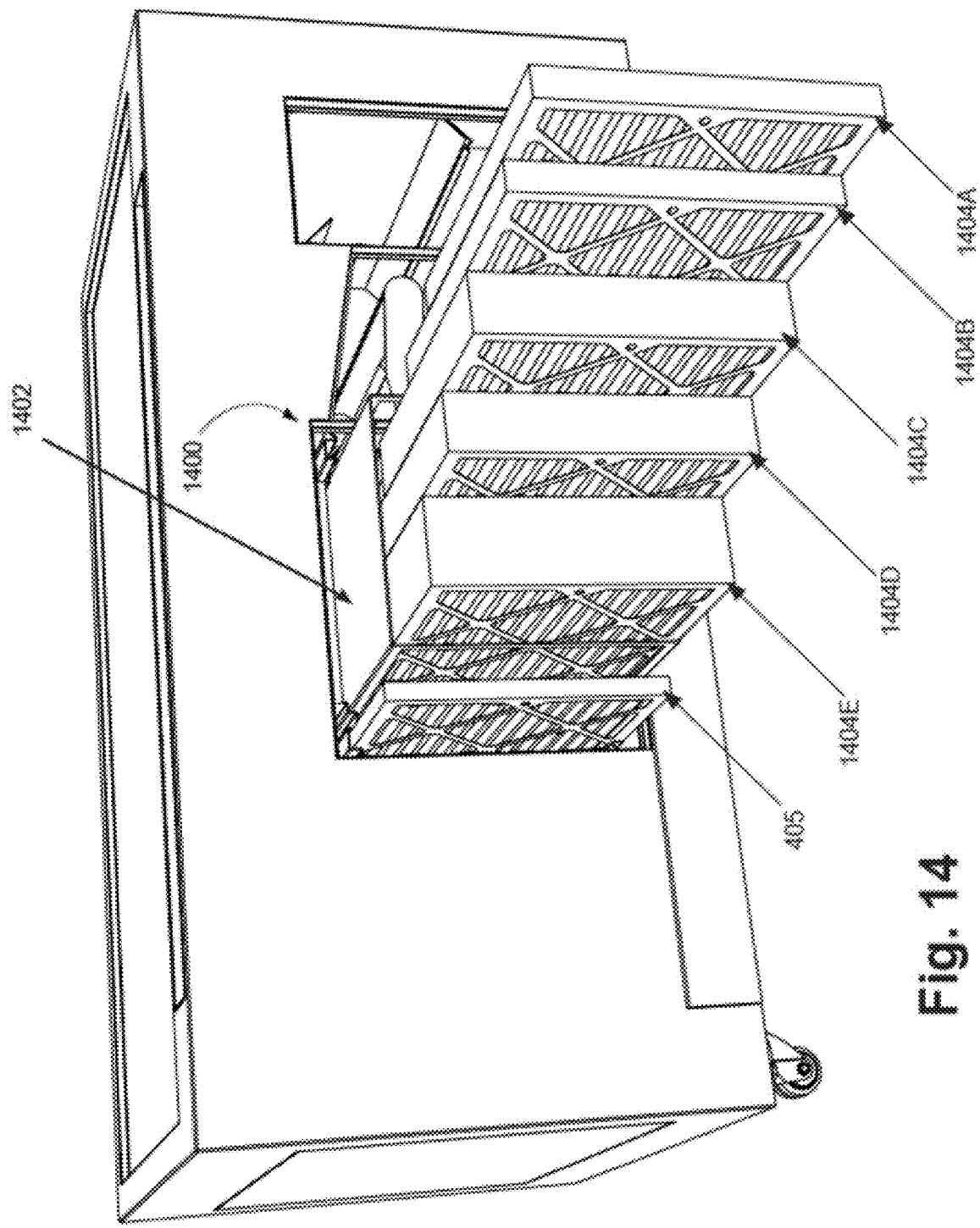
FIGS. 14-15 show aspects of an example particulate removal stage that includes a sequential filter cassette having individually removable filters.

FIG. 14 depicts an example particulate removal stage 1400 comprising a removable sequential filter cassette 1402 having a plurality of HEPA filters 1404A-1404E (or other suitable filters) that are removable from the cassette 1402 by a user. In this example, a first filter 1404A and a second filter 1404B each takes the form of a washable metal mesh filter configured to remove airborne grease particulates from the exhaust, which may help to improve absorption by other downstream filters 1404C-1404E. A third filter 1404C and a fourth filter 1404D each takes the form of a washable and/or disposable glass fiber filter configured to trap airborne particulate matter. A fifth filter 1404E takes the form of a disposable small micron paper filter configured to trap airborne particulate matter not captured by the third 1404C and fourth 1404D filters. FIG. 14 also shows a charcoal filter 405 positioned downstream of the cassette 1402, which may help to reduce odor of the exhaust. In other examples, a removable sequential filter cassette 1402 may include any other suitable number and type of filters.

Figure 15:
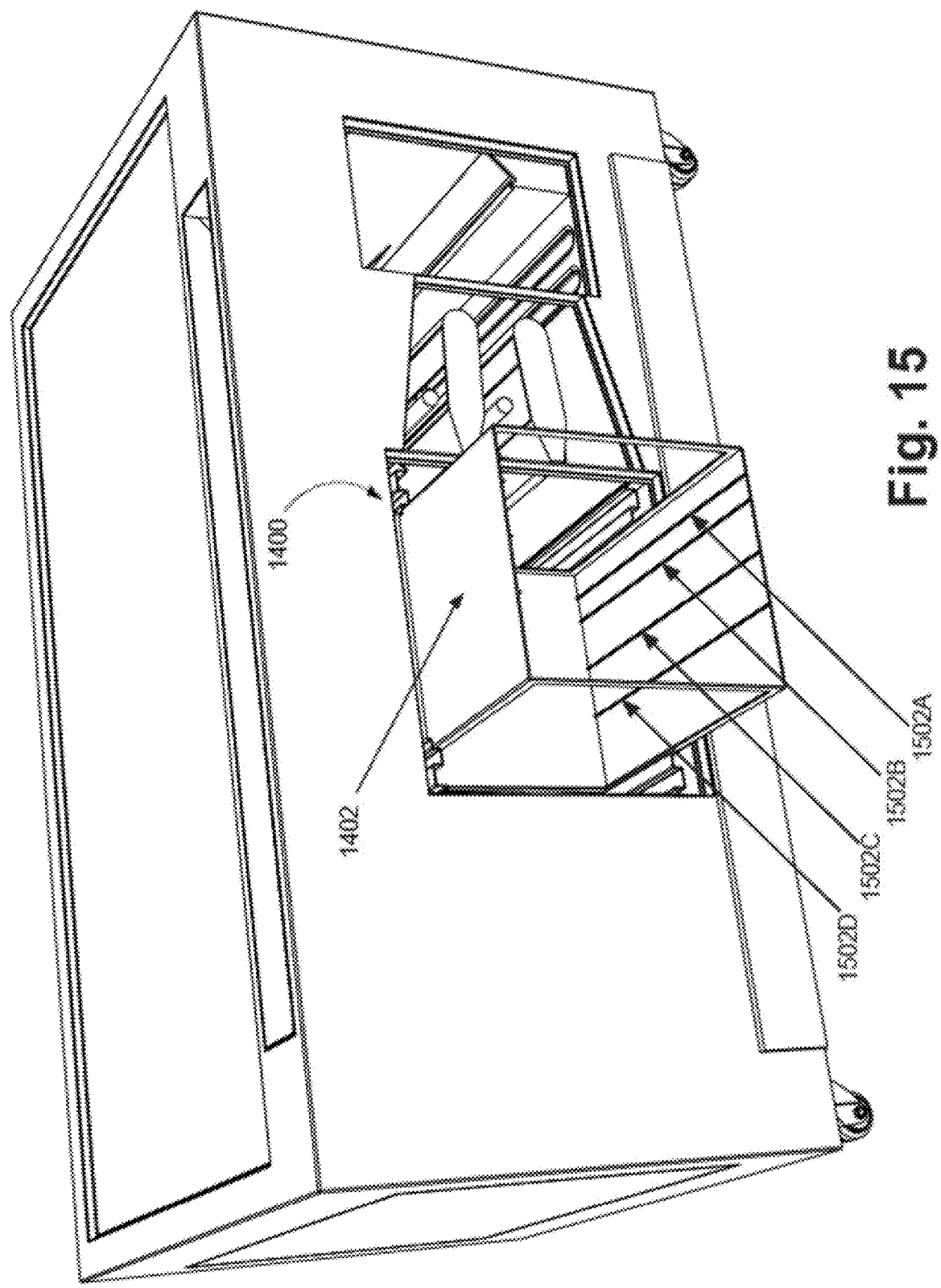

The cassette 1402 functions as a racking system for supporting the filters 1404A-1404E within the ventilation duct. In addition to the filters 1404A-1404E being removable from the cassette 1402 for servicing, the cassette 1402 is removable from the ventilation duct. FIG. 15 shows the cassette 1402 being retracted from the particulate removal stage 1400 of the ventilation duct, e.g. for cleaning of the cassette 1402 and/or the interior of the ventilation duct. In other examples, the cassette 1402 may be omitted, and racking features for filters may be formed directly in interior surfaces of the exhaust duct of a cooking system.

In the example of FIGS. 14-15, the cassette comprises a plurality of filter placement features 1502A-1502D for supporting the filters 1404A-1404E (FIG. 14) within the cassette 1402. In FIG. 15, the filter placement features 1502A-1502D take the form of physical dividers on a floor of the cassette 1402, which may help to improve serviceability and prevent incorrect filter placement. In some examples, the filter placement features 1502A-1502D may each comprise features configured to ensure that each filter 1404A-1404E is a correct filter and positioned correctly. Example features include dimensions (e.g. each filter may have a different thickness to fit in a placement feature of a corresponding dimension), a key structure complementary to a corresponding key structure on a filter, etc.

The cassette 1402 also may include one or more sensors that provide input to an interlock system for controlling operation of the ventilation system. For example, the interlock system may use information received from the sensor(s) to ensure that each filter 1404A-1404E is a correct filter for the cassette 1402 and/or correctly positioned within the cassette 1402 before allowing the ventilation system to operate. As one example, the filter placement features 1502A-1502D may include a radio frequency identification (RFID) reader to read a corresponding RFID tag on a corresponding filter 1404A-1404E. Other example sensors include optical sensors and magnetic sensors.

As mentioned above, the cooking system 100 includes a fan positioned downstream of the particulate removal system 400. Any suitable fan may be used. For example, the fan may take the form of a blower wheel fan (e.g. a squirrel cage fan) that draws air in along an axial direction relative to the blower motion, and exhausts the air in a direction tangential to the blower wheel motion.

Various aspects of the cooking system 100 may help to mitigate noise by reducing obstructions in the ventilation duct 106 upstream of the fan. As mentioned above, the inclusion of air foils and/or an increasing cross-sectional area of the ventilation duct in the UV treatment stage may mitigate noise. Noise reduction may additionally or alternatively be achieved by selectively modulating a speed of the fan. For example, the fan may take the form of a digital Modbus fan operatively coupled to a control system configured to modulate a speed of the fan. The fan speed may be modulated based upon any suitable characteristic. For example, the control system may be configured to modulate the speed of the fan based upon one or more of an inlet air temperature, an operational state of the cooking element, a measured airflow characteristic, and/or acoustics. In one example use scenario, the control system may detect that a temperature of the cooking surface 104 is at or above a threshold temperature and/or that the cooking system is operational from a cooking standpoint, and control the fan speed to operate at a suitably high speed. Likewise, when the cooking element is determined to be powered off and/or a reduced cooking surface temperature is detected, the control system may modulate the fan speed to reduce the volume of air moved by the fan. This may help to reduce airflow noise when the cooking system 100 is not being used, and thus may help to create a quieter cooking environment for an operator and/or a customer.

Figure 8:
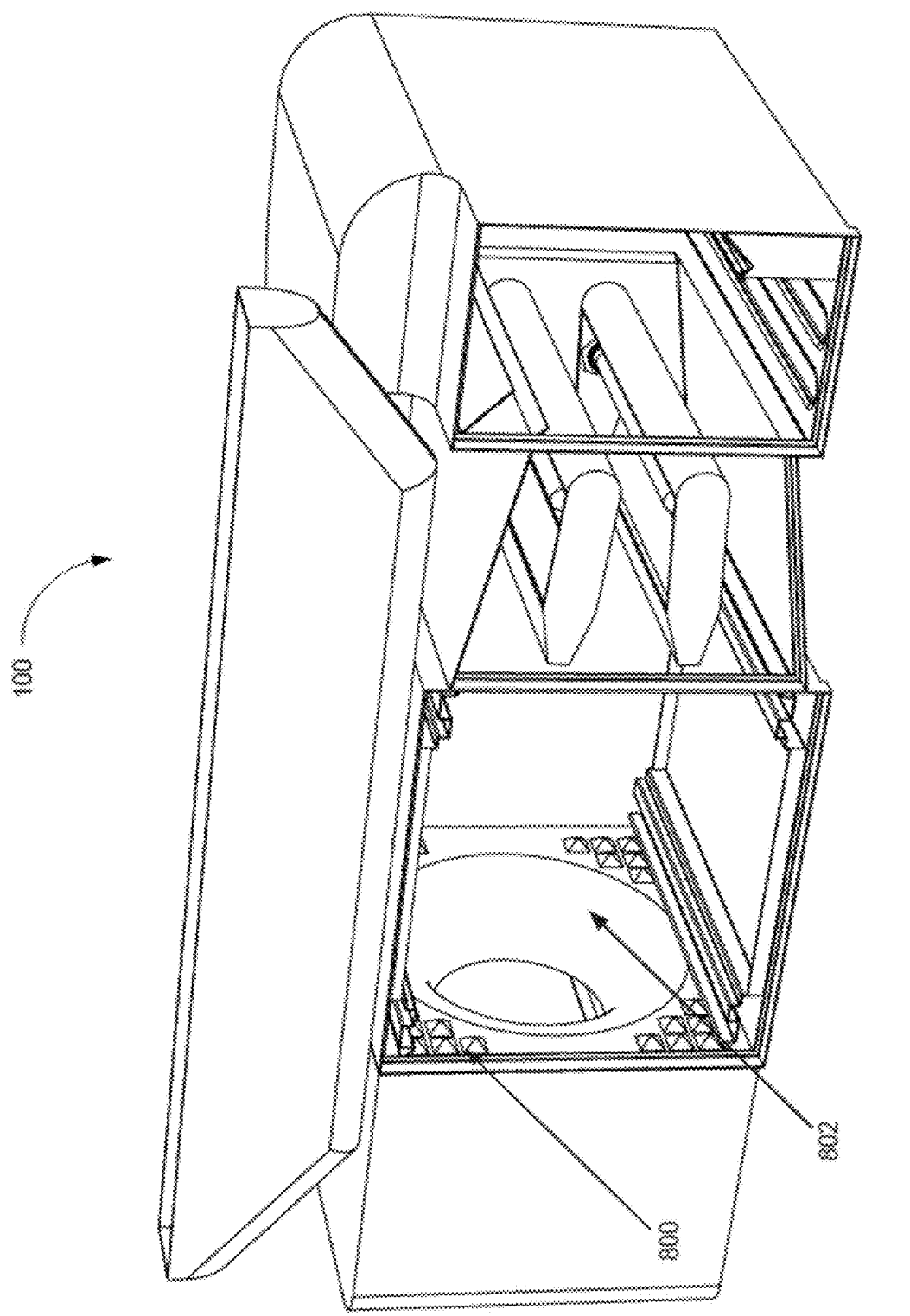
FIG. 8 shows examples of a fan inlet and acoustic interference structures within the ventilation duct.

The cooking system 100 also may implement one or more other acoustic dampening techniques proximate to and/or downstream of the fan. For example, a cooking system may include interference features inside a ventilation duct 106, to help create destructive interference among sound waves within the ventilation duct. The term "interference features" as used herein encompasses acoustic dampening structures formed from a same or different material than the ventilation duct 106, and may be embossed in, adhered to, or otherwise formed within the ventilation duct 106. In the example of FIG. 8, a wall of the ventilation duct includes a plurality of example interference features 800 proximate to an inlet of the fan 802. In this example, each interference feature 800 comprises a square pyramid shape with triangular facets on each side. In other examples, interference features 800 of any other suitable shape to help mitigate airflow noise may be used. Further, interference feature 800 may also be located in a region of the ventilation duct other than at or near the fan inlet 802, in various examples.

Figure 9:
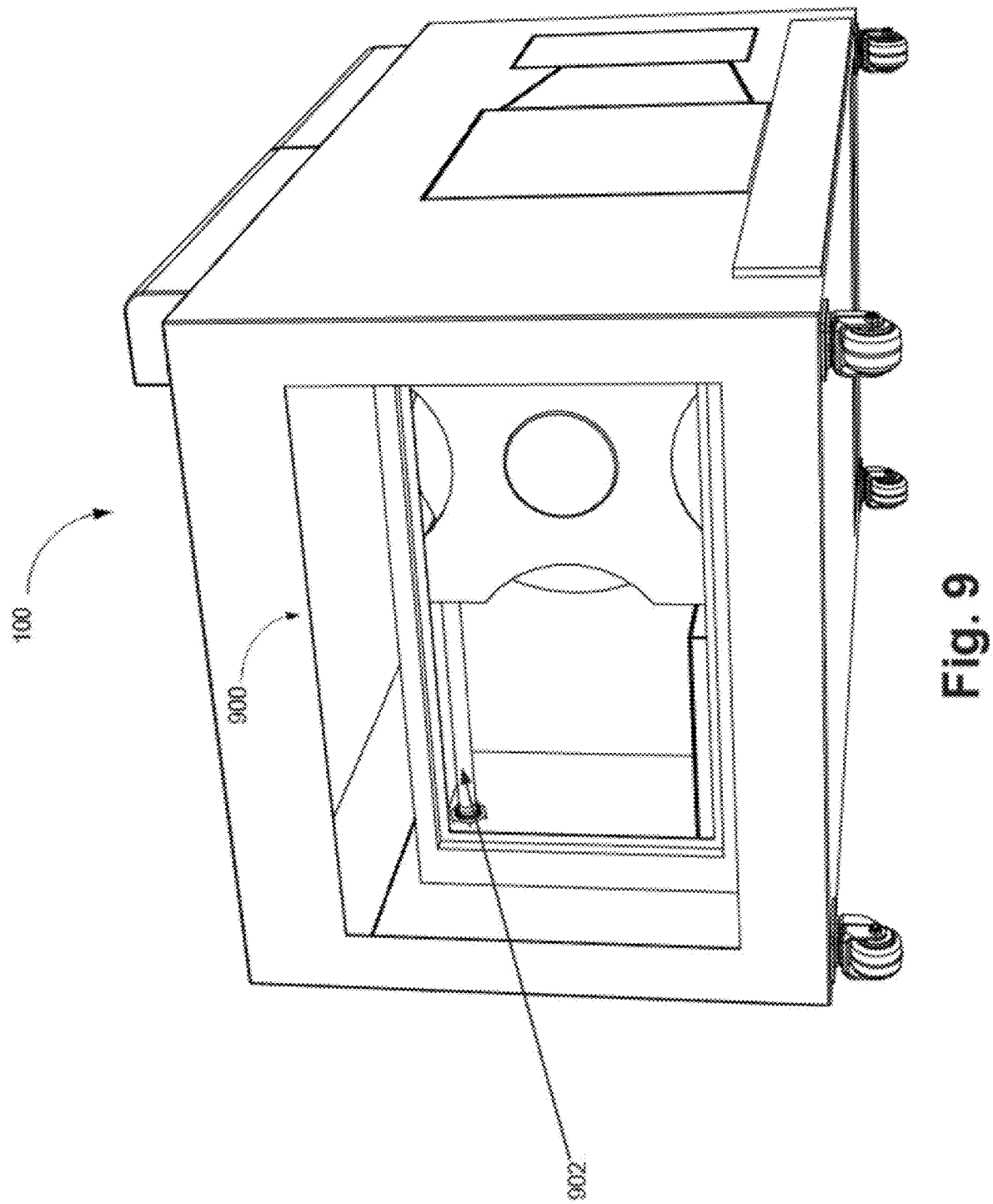
FIG. 9 shows an example UV lamp positioned in the ventilation duct downstream of the fan of FIG. 8.

The cooking system 100 further may include an ozone control system positioned downstream of the fan to help reduce ozone concentrations, including ozone released by the ESP 404, within the exhaust. When included, the ozone control system may comprise one or more UV lamps configured to output one or more wavelengths of light in the ultraviolet wavelength range. Any suitable wavelength range may be used. In some examples, the wavelength range is selected to be germicidal UV light (UV-C light). In one specific example, the ozone control system may include a UV lamp configured to output UV light having a wavelength of 253.7 nm. FIG. 9 depicts an example ozone control system 900 comprising a third UV lamp 902 positioned downstream, at a discharge side, of the fan.

Figure 10:
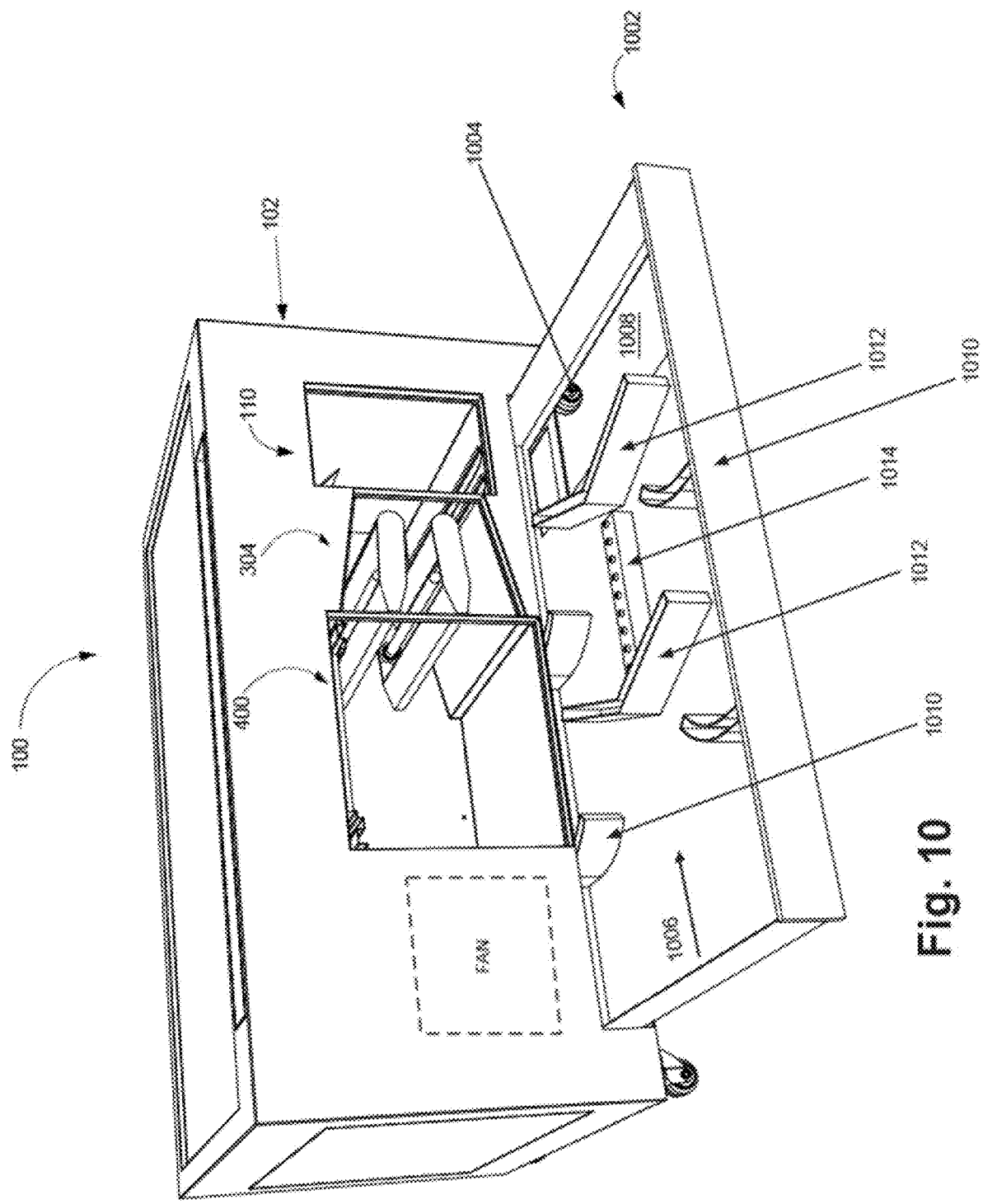
FIG. 10 shows aspects of an example chamber of a ventilation duct for noise reduction and air filtration.

Downstream of the fan, cleaned exhaust flows downwardly into an adjacent chamber. FIG. 10 shows an example adjacent chamber 1002 in the form of a drawer coupled to the body and slidably removable (e.g. via wheels 1004) from beneath the body 102. In other examples, access to the adjacent chamber 1002 may be provided in any other suitable manner.

The chamber 1002 includes a lateral flow passage 1006 and one or more muffling features, such as a noise-dampening baffle 1010, located in the lateral flow passage to help dampen noise. A noise-dampening baffle is a passive sound absorber formed, for example, from a soft and/or plush material, or a material otherwise having acoustic dampening characteristics. The noise-dampening baffle 1010 also may have filtration characteristics to help remove any additional grease, odor molecules, and/or particulate matter from the exhaust flow. Examples of noise-dampening baffles 1010 include zeolite pillows (which can also help trap and oxidize small molecules), acoustic foam, and acoustic fabric panels.

In the example shown in FIG. 10, the noise-dampening baffles 1010 each comprise a semi-circular shape. Further, the noise-dampening baffles 1010 are positioned on opposing sides of the later flow passage along a direction of airflow. In this example, the semi-circular shape may help to direct airflow along the lateral flow passage 1006 without introducing turbulence or otherwise obstructing the airflow. In other examples, a noise-dampening baffle 1010 may comprise any other suitable shape and arrangement within the chamber 1002.

In some examples, the one or more muffling features may also comprise activated charcoal, which may help gather airborne VOCs and ozone as well as dampen noise. For example, the chamber may include one or more charcoal carbon trays 1012 positioned along the lateral flow passage 1006, to filter air and dampen airflow noise as the air flows along the lateral flow passage.

In various examples, the one or more muffling features 1010 and/1012 comprise consumable materials configured to be replaced occasionally. A chamber 1002 configured to slide outwardly from the fan compartment section or otherwise allow an operator to access contents of the chamber may help to more easily replace such consumables.

In some examples, the cooking system 100 also may include one or more ozone mitigation components to further clean the air and deplete ozone before the air is discharged into the surrounding cooking environment. In the example of FIG. 10, the one or more ozone mitigation components comprises an ion generator 1014. Without wishing to be bound by theory, the ion generator 1014 may deplete ozone by producing hydrogen peroxide as an intermediary species by the reaction between water and oxygen: $2H_2O+O_2 \rightarrow H_2+H_2O_2+O_2$. The hydrogen peroxide may, in turn, react with and break down ozone to form oxygen and hydroxyl radicals: $H_2O_2+2O_3 \rightarrow 3O_2+2OH$. Any suitable ion generator may be used. For example, the ion generator 1014 may take the form of a bipolar ion generator 1014 configured to generate cationic and ionic species that further treat the cleaned exhaust. As a more specific example, the ion generator may take the form of a bipolar needlepoint ionizer having a sharply textured surface, and may be positioned to release ions into a baffled or an attenuation chamber before discharge air is recirculated into an occupied space. In the depicted example, the ion generator 1014 is positioned downstream of the fan, in the chamber 1002. In other examples, an ion generator may be positioned at any other suitable stage of a ventilation system, pre- and/or post-fan.

The one or more ozone mitigation components further may include an ozone reduction catalyst, in addition or alternatively to an ion generator. Any suitable ozone reduction catalyst may be used. One example of a suitable ozone reduction catalyst is CARULITE 400 (available from Cams Corp. of Peru, IL), which may catalyze the reduction of ozone to molecular oxygen at relatively lower temperatures. When included, an ozone reduction catalyst may be applied to an interior surface of the ventilation duct and/or the chamber 1002. In some examples, a surface of the ventilation duct and/or chamber comprises a coating of the ozone reduction catalyst. In other examples, the ozone reduction catalyst may be supported in the ventilation duct and/or chamber on a support material, which may be removable from the cooking system for replacement or servicing. Examples of support materials for supporting an ozone reduction catalyst within the ventilation duct and/or chamber include polymeric (e.g. a foam), paper, and metal materials.

The adjacent chamber 1002 further includes a discharge opening 1008 after the lateral flow passage 1006, where filtered air is discharged out of the adjacent chamber 1002 and into a surrounding environment of the cooking system. In the example shown in FIG. 10, the discharge opening 1008 discharges filtered air downwards towards a floor supporting the cooking system. In other examples, filtered air may be discharged from a side of the adjacent chamber 1002 (e.g. in a direction of airflow along the lateral flow passage 1006). Further, while depicted as a single opening in FIG. 10, the discharge opening 1008 may comprise a patterned opening (slotted, mesh, etc.) in other examples.

As mentioned above, the ventilation duct interior may comprise radiused interior corners to facilitate cleaning compared to a duct having sharp corners. In some examples, each radiused edge may have a radius of curvature greater than ¾", and in some examples greater than ½". In any instance, a radiused edge may help to improve sanitation, as less grease and other matter may become trapped in a radiused edge compared to an angled edge. Further, a radiused edge provides a smooth surface that may more easily be wiped cleaned by a user than an angled edge.

Figure 11:
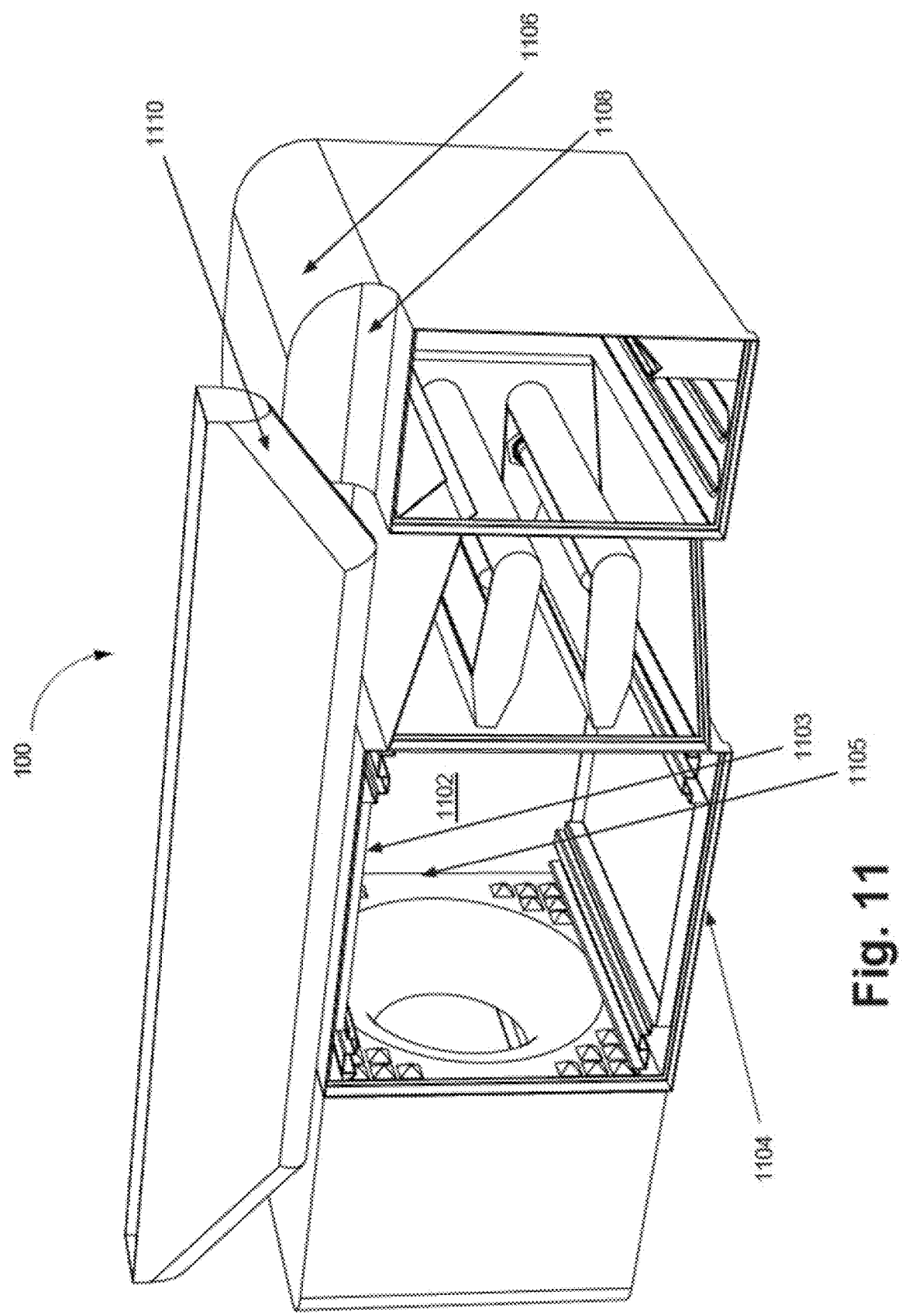
FIG. 11 shows examples of radiused internal corners and adjoining transition sections of a ventilation duct.

FIG. 11 illustrates example internal edges of a ventilation duct interior that are radiused rather than angled. In this example, corners of a duct wall 1102 are radiused along a top edge where the wall 1102 meets the ceiling 1103 and along a bottom edge where the wall 1102 meets the floor 1104 of the ventilation duct. Other interior regions of the ventilation duct may also include radiused edges. As other examples, an interface 1105 between the front wall 1102 (and/or rear wall) and an inlet of a fan, an interface 1106 between an inlet aperture and a grease filtration stage 110, and portions 1108 and/or 1110 of the inlet aperture may be radiused. In other examples, various external edges of a cooking system also may be radiused rather than angled.

As mentioned above, a cooking system may include an inlet aperture or ventilation hood extending the length of the cooking appliance or in some examples beyond the length of the cooking appliance to ensure capture of cooking odor and grease laden vapors. The design of the inlet aperture may help to guide smoke generated during cooking into the ventilation duct. A unitary inlet aperture that extends the entire length of the cooking appliance may be cumbersome to clean, as it may not fit within a dishwasher and thus require hand washing. Accordingly, an inlet aperture may include two or more sections, each extending a portion of the length of the inlet aperture. Each section may be sized to fit inside a dishwasher, in some examples, which may help to improve sanitation of the inlet aperture. Further, each inlet aperture section may be of equal or unequal length.

Figure 12:
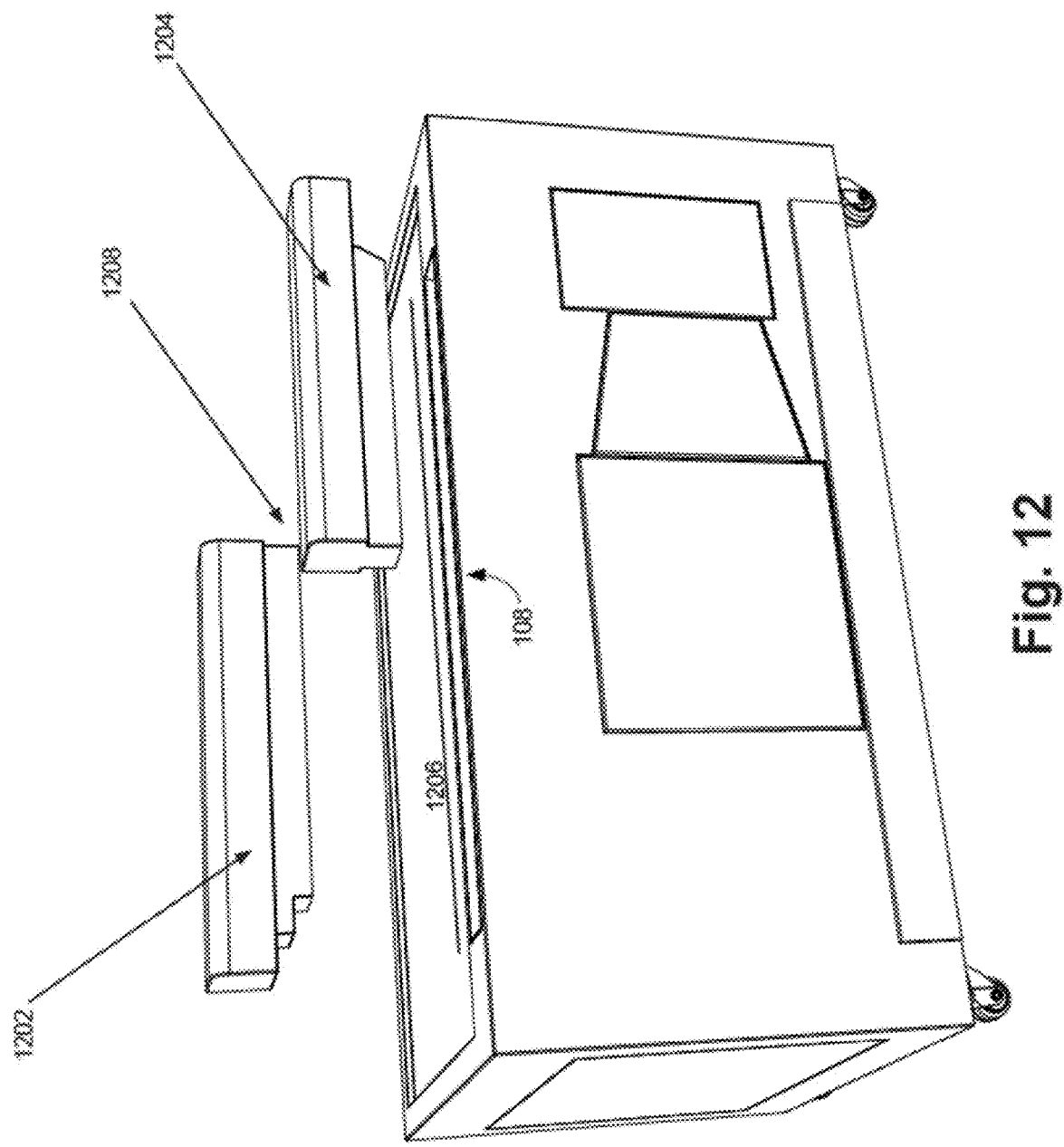
FIG. 12 shows an example of an inlet aperture comprising two removable sections.

FIG. 12 depicts an example inlet aperture 108 comprising a first section 1202 and a second section 1204 that each extends a portion of a length 1206 of the inlet aperture 108. The first inlet aperture section 1202 and the second inlet aperture section 1204 meet at a junction 1208. In some examples, the first inlet aperture section 1202 and second inlet aperture section 1204 are fit together at the junction 1208 to form a continuous inlet aperture, e.g. via an interference fit, a frictional fit, a plug/slot mated connection, etc. In other examples, one or more of the first inlet aperture section 1202 and the second inlet aperture section 1204 may be closed at the junction 1208, e.g. via a cap or other sidewall.

Figure 13:
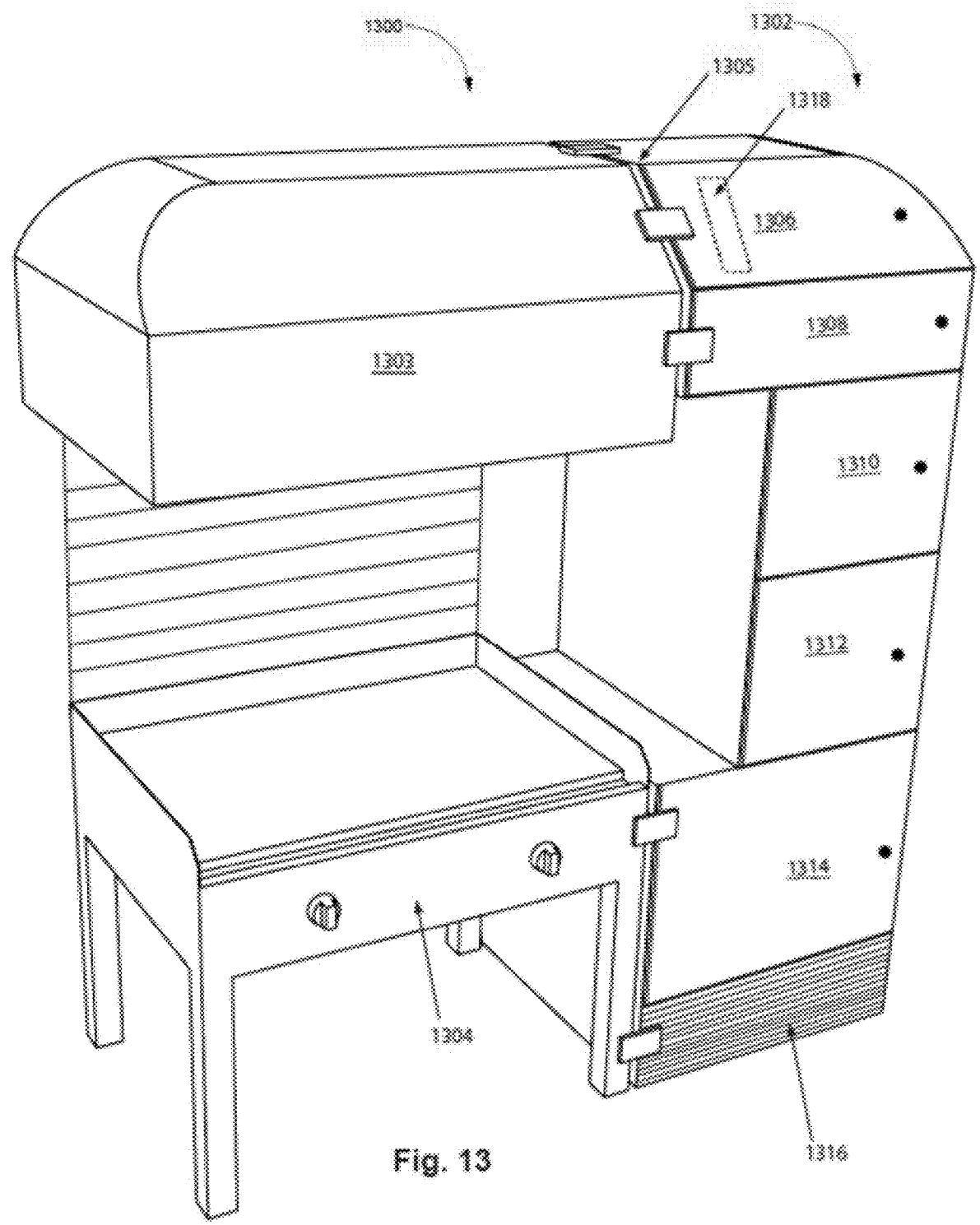
FIG. 13 depicts an example vertically oriented recirculating ventilation module that is adaptable for use with a variety of cooking appliances.

Aspects of a recirculating ventilation system as disclosed herein may be implemented in other contexts than a teppanyaki-style grill. For example, restaurants may utilize a variety of different types of cooking equipment, each of which may require ventilation. As installing such ventilation may be expensive and require roof modifications, providing internal recirculating ventilation for such cooking systems may pose advantages. FIG. 13 depicts an example of a modular recirculating ventilation system 1300 that is adaptable for use with a variety of different types of cooking appliances. While aspects of the system 1300 are depicted as being stacked vertically in FIG. 13, the aspects of system 1300 may be arranged in a horizontal fashion in other examples.

The system 1300 includes a ventilation duct 1302 configured to ventilate exhaust from a cooking appliance 1304. In the example of FIG. 13, the ventilation duct 1302 is configured to attach to a ventilation hood 1303 disposed above a cooking component of the cooking appliance 1304 via a fire-proof coupling 1305. Any suitable cooking appliance comprising any suitable cooking component may be used. In FIG. 13, the cooking appliance 1304 comprises a griddle and the cooking component comprises a grill surface of the griddle. Other examples of cooking appliances include ovens, fryers, ranges, grills, and broilers. Other examples of cooking components include a heated reservoir (e.g. oil reservoir), a heated chamber (e.g. interior chamber of an oven), a cooking rack disposed beneath a broiler, etc.

In the example of FIG. 13, the over-appliance ventilation hood 1303 functions as an inlet aperture for the system 1300. In other examples, the ventilation duct 1302 may comprise an inlet aperture configured to capture smoke from a cooking appliance, or may comprise a fire-proof duct which connects to a nearby or remote cooking appliance via a fire-proof coupling disposed around a perimeter of the fire-proof duct. In a more specific example, the fire-proof coupling 1305 may attach to a fire-proof duct of an overhead or perpendicular vent hood positioned over or next to a cooking appliance. Further, the inlet aperture may be integrally attached to the ventilation duct 1302 (e.g. by coupling the cooking appliance 1304 to the ventilation duct 1302 via a draw-latch or other securing mechanism) to help ensure that the inlet aperture and ventilation duct are properly connected to capture cooking exhaust.

Downstream of the inlet aperture, the system 1300 comprises a grease filtration stage 1306 connected to an opening of the ventilation duct 1302, a UV treatment system 1308, and a particulate removal system 1310. Further, the system 1300 comprises a fan 1312 configured to pull fumes through the ventilation duct 1302, grease filtration stage 1306, UV treatment system 1308, and particulate removal system 1310, and discharge at least partially filtered exhaust into an adjacent chamber 1314 comprising muffler attenuation features before discharging filtered air into the cooking environment via a discharge air duct opening 1316. Each of these components may function as described above. Further, in FIG. 13, each of these components is depicted as being located behind an access panel or door that is fire-proof rated with locking draw-latches, which allow a user to access an interior of the ventilation duct for cleaning/servicing. In other examples, the access panels for each component may comprise any other suitable latch or locking mechanism. The use of modular system 1300 may help to facilitate the adaption of recirculating ventilation in a potentially wide variety of contexts, thereby helping to reduce the expense of installing roof-based ventilation in such contexts.

While shown as ventilating cooking exhaust from one cooking appliance in FIG. 13, the system 1300 may be configured to ventilate cooking exhaust from multiple appliances in other examples. In one specific example, the ventilation duct 1302 may be attached to a T-shaped duct comprising multiple inlet apertures, such as an inlet aperture configured to receive cooking exhaust from a deep fryer on one side of the ventilation duct and an inlet aperture configured to receive cooking exhaust from a broiler on an opposing side of the ventilation duct.

As mentioned above with regard to FIG. 1, a cooking system according to any of the examples described herein may also include a water spray system configured to reduce a temperature of an inlet air stream in the ventilation duct by injecting a spray of cold water into the inlet air stream. FIG. 13 depicts another implementation of a water spray system 1318. Controlling inlet air temperature may help to maintain proper performance of a downstream filter(s). When included, the water spray system may comprise one or more spray nozzles disposed in the ventilation duct, e.g. at the inlet aperture or downstream of the inlet aperture, and a controller to control the spray of water. In some examples, a temperature sensor (e.g., thermocouple, resistance temperature detector (RTD), etc.) may be disposed in the ventilation duct to measure inlet air temperature. In examples that are temperature controlled, when the temperature is above a threshold temperature, the controller controls the one or more spray nozzles to inject cold water into the inlet air stream. In some examples, more than one threshold may be applied, e.g. for a hysteretic effect. In such examples, a first threshold may be used to trigger operation of the water spray system. When the temperature is equal to or less than a second threshold temperature (e.g., the inlet air temperature is determined to be sufficiently cool) that is lower than the first threshold, the controller then disengages water spray injection. In some more specific examples, the first threshold has a value within a range of 90 to 100 degrees Fahrenheit (F), and the second threshold temperature has a value within a range of 60 to 70 degrees F. In other examples, such a temperature sensor may be omitted, and the water spray system may be controlled manually.

In some examples, the water spray system may deliver cold water from a cold tap water supply to the one or more spray nozzles based upon the measured temperature and a measurement indicating a presence of available water (e.g., a water pressure measurement, water level measurement, etc.). Further, in some examples, the cold water (e.g., between 33 degrees F. and 95 degrees F.) may undergo a process to include a dissolved ozone concentration in the cold water supply, which may help to remove VOCs from the inlet airflow. In one specific example, the dissolved ozone concentration comprises at least 0.2 mg/L (milligrams per liter) parts per million (ppm) and less than or equal to 8 mg/L (ppm). The water spray system may further comprise a water collection system to capture water that was not vaporized or condenses out of the exhaust. The water collection system may include, for example, one or more baffles to collect the water not vaporized and a water storage tank(s) to store the water collected at the baffle(s). In some examples, the water collection system includes a sensor configured to sense when a water storage tank reaches its capacity, and to trigger draining of the water storage tank, whether by triggering an automatic mechanism or by triggering the output of an alert to perform a manual draining.

The controller may also be configured to control the water spray system in response to a detected fire trigger event (e.g. a detected spark, smoke, and/or fire). For example, the controller may be operatively coupled to a fire suppression system switch to sense (or be alerted to) a fire trigger event and engage cold water spray. If a fire trigger event activates a fire suppression system of the cooking system, the controller may control the water spray system to spray water from the one or more nozzles, to assist with fire suppression at/within the inlet aperture of the ventilation duct.

In some examples, the water spray system may include a condensate pan and/or an evaporator coil, which may help to reduce or prevent the discharge of water vapor into an occupied space. In some such examples, the water spray system may also include a moisture sensor configured to measure a content of water vapor within the ventilation duct. In instances in which the water spray system inadvertently creates an excess of steam and/or water vapor, e.g. as measured by the moisture sensor, the evaporator coil and/or condensate pan may help to remove moisture from the airflow and collect condensation such that excess water vapor is not discharged from the recirculating ventilation system into an occupied space.

Figure 16:
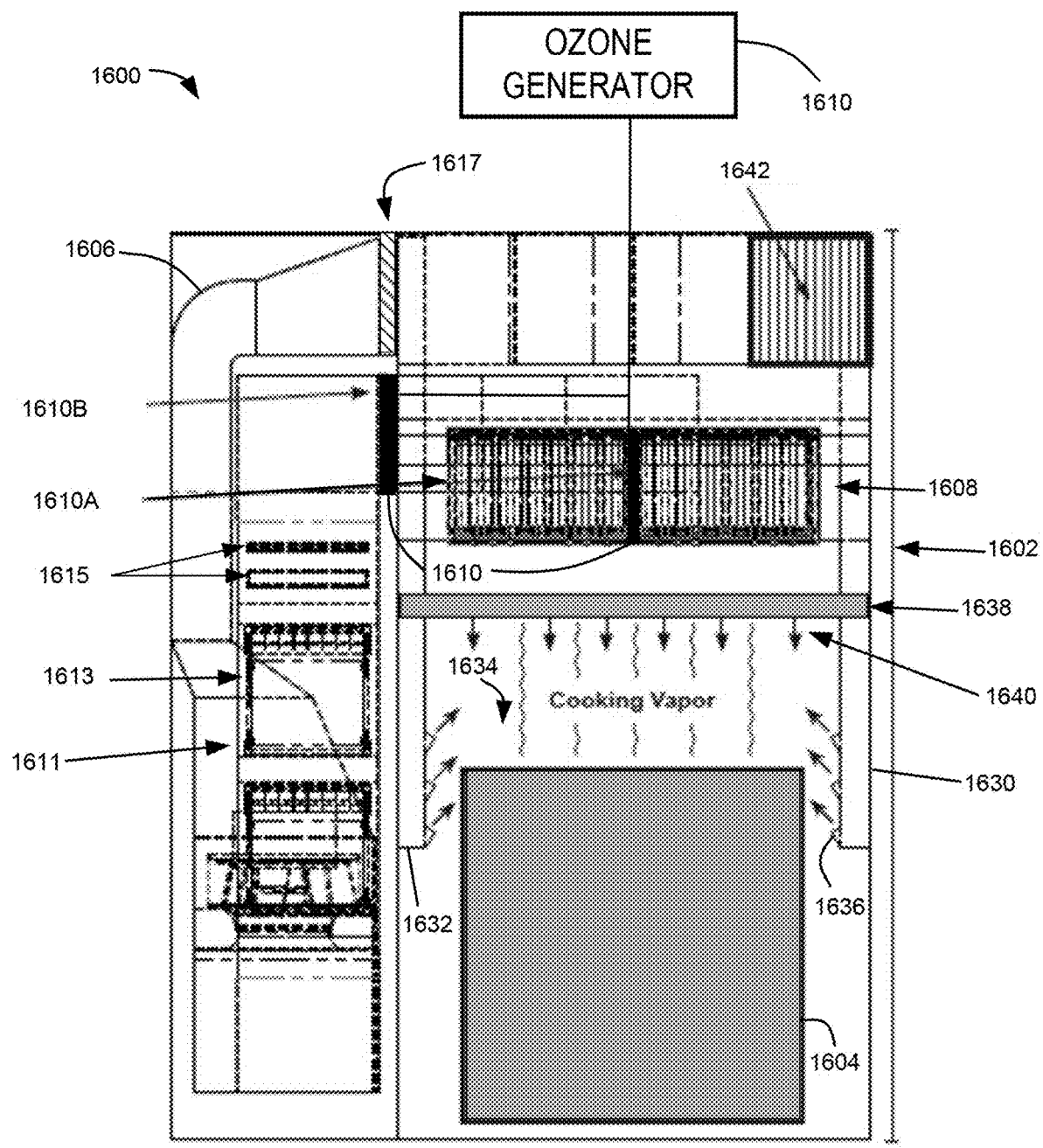
FIG. 16 shows another example cooking appliance ventilation system.
Figure 17:
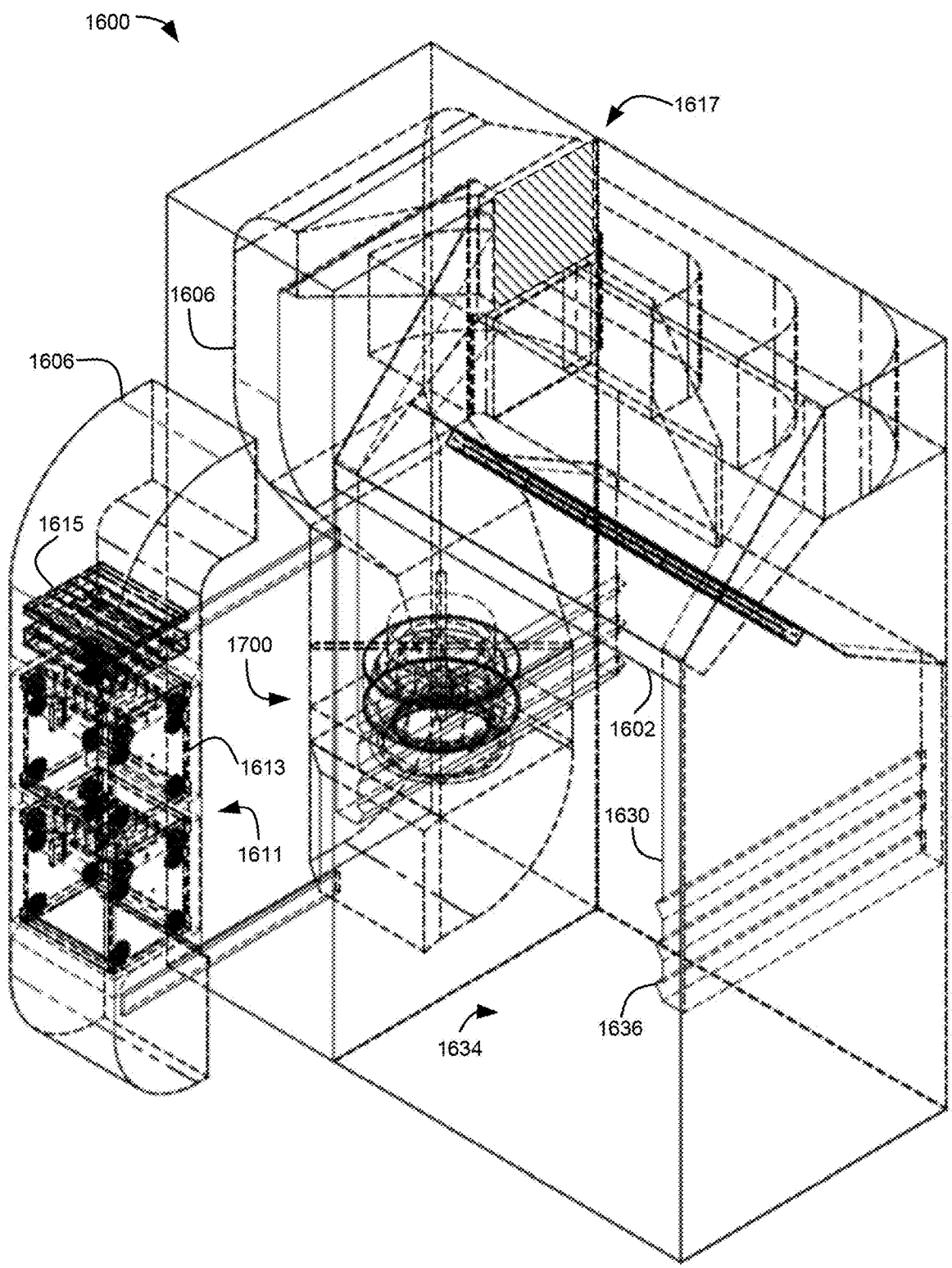
FIG. 17 shows a perspective schematic view of the cooking appliance ventilation system of FIG. 16, and illustrates example internal components.

FIG. 16 shows another example recirculating cooking appliance ventilation system 1600. Cooking appliance ventilation system 1600 comprises a hood 1602 configured to be positioned at least partially over a cooking appliance 1604. Cooking appliance ventilation system 1600 further comprises a ventilation duct 1606 connected with the hood 1602. The ventilation duct 1606 extends along a path that travels downwardly along a side of the cooking appliance 1604, and then upwardly along the side of the cooking appliance 1604 to various options for outlets, as described in more detail below. FIG. 17 shows a perspective view of cooking appliance ventilation system 1600, with a portion of the ventilation duct 1606 broken away and with example interior components shown.

Continuing with FIGS. 16-17, the cooking appliance ventilation system 1600 comprises one or more baffles 1608 positioned within the hood 1602. The baffles 1608 may be configured to condense grease from a flow of cooking exhaust, thereby removing at least some grease from the cooking exhaust. The cooking appliance ventilation system 1600 further comprises an ozone generator, shown schematically at 1610. The ozone generator 1610 is configured to generate ozone for introduction into the flow of cooking exhaust through the ventilation duct 1606. Ozone may be introduced into the ventilation duct 1606 at any suitable location. In the depicted example, ozone may be introduced into the ventilation duct 1606 downstream of baffles 1608 via a first ozone injector 1610A, and at or close to an inlet of the ventilation duct 1606 at a second ozone injector 1610B, where the ventilation duct 1606 joins to the hood 1602. In other examples, ozone alternatively or additionally may be introduced into the ventilation duct 1606 at a location farther from the inlet of the ventilation duct.

FIG. 17 illustrates a fan 1700 located within an interior of the ventilation duct 1606. The fan 1700 is configured to pull cooking exhaust through the hood 1602 and move the exhaust through the ventilation duct 1606. FIGS. 16 and 17 further show a filtration stage 1611. Filtration stage 1611 may comprise any suitable components for removing cooking byproducts from the cooking exhaust. For example, filtration stage 1611 may comprise one or more of an electrostatic precipitator 1613 and/or one or more particulate filters 1615. In the depicted example, ozone is injected into the ventilation duct upstream of the fan 1700. In other examples, ozone alternatively or additionally may be injected into the ventilation duct between the fan 1700 and the filtration stage 1611. In yet other examples, ozone alternatively or additionally may be injected into the ventilation duct downstream of the filtration stage 1611. Further, while the fan 1700 is depicted upstream of the filtration stage 1611 in FIG. 17, in other examples a fan may be positioned downstream of a filtration stage, or between filtration stages.

Continuing with FIGS. 16 and 17, cooking appliance ventilation system 1600 further includes one or more ozone mitigation components positioned downstream of the ozone source. The one or more ozone mitigation components are configured to remove residual ozone from within the ventilation duct 1606 before cleaned air is vented from the ventilation duct 1606. In the depicted example, the one more ozone mitigation components comprises an ozone reduction catalyst 1617 arranged in the ventilation duct downstream of the fan 1700 and filtration stage 1611. In other examples, an ozone reduction catalyst may be located at any other suitable location within a ventilation duct. For example, an ozone reduction catalyst alternatively or additionally may be located in the filtration stage 1611, upstream of the filtration stage 1611, and/or upstream of the fan 1700. The term "ozone reduction catalyst" as used herein refers to any material that catalyzes a chemical change in ozone to another molecule, such as molecular oxygen.

Figure 18:
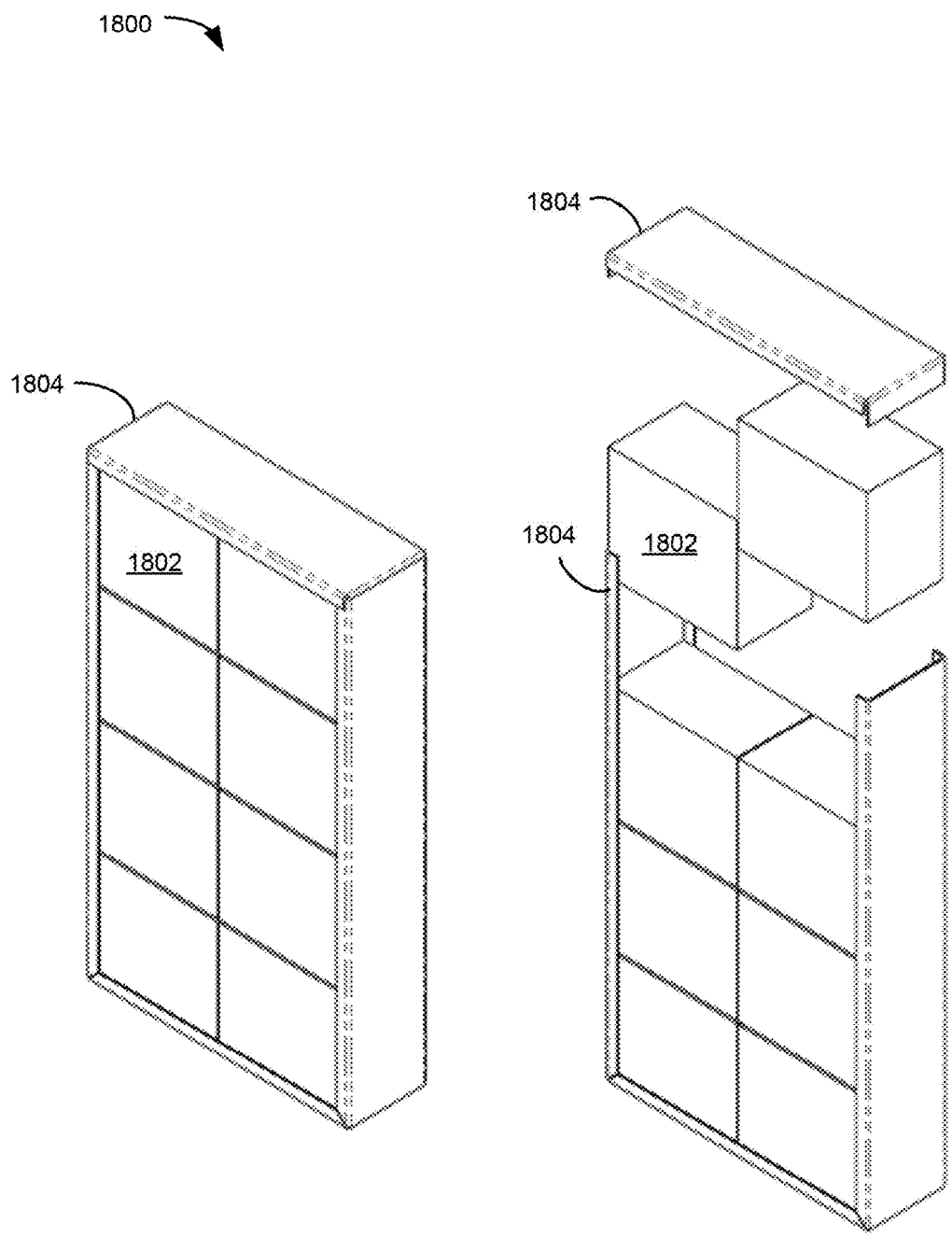
FIG. 18 shows an example ozone reduction catalyst comprising a plurality of catalyst units held within a catalyst holder.

Ozone reduction catalyst 1617 may take any suitable form. In some examples, ozone reduction catalyst 1617 may have a monolithic form, such that a single catalyst structure (e.g. porous substrate coated with one or more catalytically active materials) fills substantially a cross-sectional area of the ventilation duct interior. In other examples, an ozone reduction catalyst may be formed from a plurality of catalyst units that are arranged within a ventilation duct to reduce ozone concentrations in the ventilation duct. In such examples, each catalyst unit occupies a portion of a cross-sectional area of the ventilation duct. FIG. 18 shows an example ozone reduction catalyst 1800 comprising a plurality of catalyst units 1802 arranged in a catalyst holder 1804. In the depicted example, each catalyst unit has a rectangular brick form. In other examples, catalyst units may have any other suitable shape. Examples include units with cubic and hexagonal cross-sectional shapes. In yet other examples, catalyst units of different shapes may be arranged within a catalyst holder. Forming a catalyst structure from a plurality of catalyst units arranged may provide for lower manufacturing costs than forming a larger, monolithic catalyst structure. The catalyst holder 1804 may allow the catalyst units to be arranged in a configuration to form a wall that substantially fills a cross-sectional area of the ventilation duct and then installed as a unit, thereby simplifying manufacturing of the cooking appliance ventilation system 1600.

A cooking appliance ventilation system may be configured to output cleaned air from any suitable location. In some examples, cleaned air may be vented at a location above or behind a hood. In other examples, cleaned air may be vented in a manner that helps to direct cooking exhaust from a cooking appliance toward a hood. Returning to FIGS. 16-17, cooking appliance ventilation system 1600 comprises a first outlet duct 1630 and a second outlet duct 1632 each positioned along lateral sides of a cooking appliance space 1634 located beneath the hood 1602. First outlet duct 1630 and second outlet duct 1632 each deliver cleaned cooking exhaust to outlets 1636. Outlets 1636 are positioned to blow cooking exhaust from a cooking appliance toward the hood 1602 and the inlet aperture of the ventilation duct 1606.

Further, the cooking appliance ventilation system 1600 also comprises a third outlet duct 1638 formed in or located adjacent to a lower edge of the hood 1602. The third outlet duct 1638 is configured to direct cleaned cooking exhaust out of outlets 1640. Outlets 1640 are configured to direct the cleaned cooking exhaust downwardly, thereby forming an air curtain that extends downwardly from the hood. The use of outlets 1636 and/or 1640 for cleaned cooking exhaust thus helps to direct cooking exhaust from a cooking appliance toward hood for cleaning. The ventilation duct 1606 further may comprise an overflow discharge register 1642 to vent cleaned cooking exhaust that does not pass through outlets 1640 or outlets 1636. The depicted cooking appliance ventilation system 1600 is configured as a separate unit from a cooking appliance and is configured to be positioned at least partially over a cooking appliance located within cooking appliance space 1634. In other examples, cooking appliance ventilation system 1600 can be integrated with a cooking appliance. Further, in yet other examples, features of cooking appliance ventilation system 1600, such as the ozone reduction catalyst, can be incorporated into tabletop cooking appliances as disclosed herein, and/or any other suitable type of cooking appliance.

Figure 19:
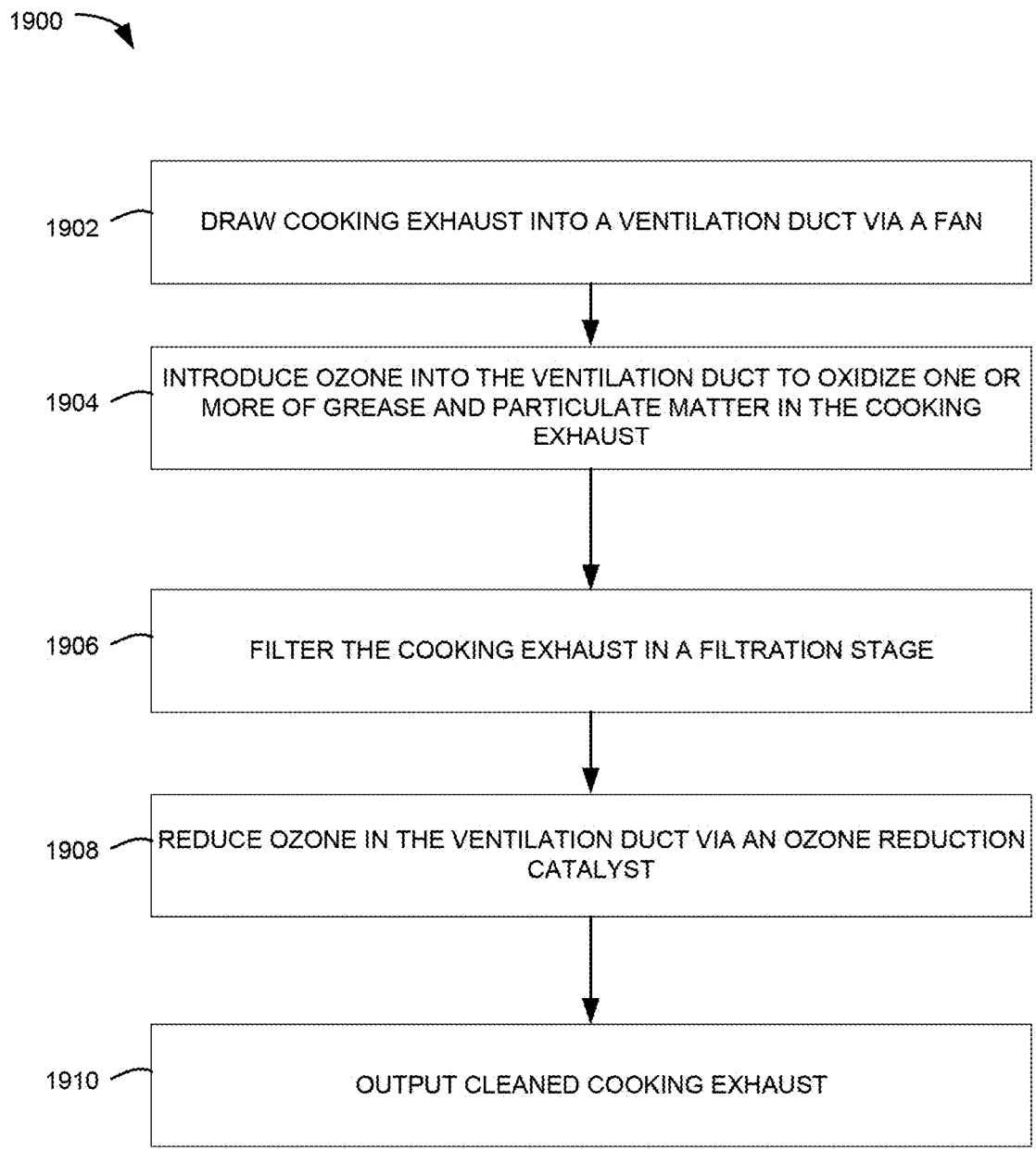
FIG. 19 shows a flow diagram depicting an example method for operating a cooking appliance ventilation system.

FIG. 19 shows a flow diagram depicting an example method 1900 for operating a cooking appliance ventilation system. Method 1900 comprises, at 1902 drawing cooking exhaust into a ventilation duct via a fan. Method 1900 further comprises, at 1904, introducing ozone into the ventilation duct to oxidize one or more of grease and particulate matter in the cooking exhaust. In some examples ozone can be introduced into the ventilation duct at a location upstream of a fan, while in other examples the ozone can be introduced at a location downstream of the fan. The ozone helps to oxidize grease and odors in the cooking exhaust, and thus helps to clean the cooking exhaust air. Method 1900 further comprises, at 1906, filtering the cooking exhaust in a filtration stage of the ventilation duct. The filtration stage may include any suitable filtration systems, such as an electrostatic precipitator and/or one more particulate filters. The filtration stage include components positioned upstream and/or downstream of the fan in various examples.

Method 1900 further comprises, at 1908, reducing ozone in the ventilation duct via an ozone reduction catalyst. This helps to remove any ozone that did not react with cooking exhaust components. In some examples, the ozone reduction catalyst may be positioned upstream of the fan, while in other examples, the ozone reduction catalyst may be positioned downstream of the fan. The ozone reduction catalyst may comprise a monolithic structure, or a plurality of catalyst units that each occupies a portion of a cross-sectional area of the ventilation duct.

Method 1900 further comprises, at 1910, outputting cleaned cooking exhaust from the ventilation system. In some examples, the cleaned cooking exhaust is output from locations that help to direct new cooking exhaust into a hood for ventilating. In such examples, one or more outlets for cleaned cooking exhaust may be positioned to blow new cooking exhaust toward the inlet aperture of the ventilation system, and/or to form an air curtain that extends downwardly from the hood.

Another example provides a cooking appliance ventilation system, comprising a ventilation duct comprising an inlet aperture configured to receive cooking exhaust, a fan configured to pull the cooking exhaust through the inlet aperture and the ventilation duct, an ozone source configured to introduce ozone into the ventilation duct, and one or more ozone mitigation components positioned within the ventilation duct downstream of the ozone source. In some such examples, the one or more ozone mitigation components alternately or additionally comprises an ozone reduction catalyst arranged in the ventilation duct. In some such examples, the ozone reduction catalyst alternately or additionally comprises a plurality of catalyst units each occupying a portion of a cross-sectional area of the ventilation duct. In some such examples, the plurality of catalyst units are alternately or additionally arranged in a catalyst unit holder. In some such examples, the ozone reduction catalyst is alternately or additionally located downstream of the fan. In some such examples, the ventilation duct is alternately or additionally configured to direct air into one or more outlets positioned to blow cooking exhaust from a cooking appliance toward the inlet aperture. In some such examples, the cooking appliance ventilation system alternately or additionally comprises a hood, wherein the ventilation duct is configured to direct air into one or more outlets that are positioned to form an air curtain that extends downwardly from the hood. In some such examples, the cooking appliance ventilation system alternately or additionally comprises an ozone generator. In some such examples, the cooking appliance ventilation system alternately or additionally comprises a hood and one or more baffles positioned within the hood at the inlet aperture, and further comprising an ozone outlet configured to introduce ozone from the ozone generator into the ventilation duct downstream of the one or more baffles. In some such examples, the cooking appliance ventilation system is alternately or additionally integrated with a cooking appliance. In some such examples, the cooking appliance ventilation system is alternately or additionally configured to be positioned at least partially over a cooking appliance.

Another example provides, a cooking appliance ventilation system, comprising a ventilation duct comprising an inlet aperture configured to receive cooking exhaust, and an ozone reduction catalyst located within the ventilation duct, the ozone reduction catalyst comprising a plurality of catalyst units arranged in a catalyst holder, each catalyst unit occupying a portion of a cross-sectional area of the ventilation duct. In some such examples, each catalyst unit alternately or additionally has a rectangular block shape. In some such examples, the plurality of catalyst units are alternately or additionally arranged in the catalyst holder to form a wall that substantially fills a cross-sectional area of a portion of the ventilation duct. In some such examples, the cooking appliance ventilation system alternately or additionally comprises an ozone generator and an ozone outlet configured to introduce ozone into the ventilation duct. In some such examples, the ventilation duct is alternately or additionally configured to direct air into one or more outlets positioned to blow cooking exhaust from a cooking appliance toward the inlet aperture. In some such examples, the cooking appliance ventilation system alternately or additionally comprises a hood, wherein the ventilation duct is configured to direct air into one or more outlets that are positioned to form an air curtain that extends downwardly from the hood.

Another example provides a method of operating a cooking appliance ventilation system, comprising drawing cooking exhaust into a ventilation duct via a fan, introducing ozone into the ventilation duct to oxidize one or more of grease and particulate matter in the cooking exhaust, filtering the cooking exhaust, reducing ozone in the ventilation duct via an ozone reduction catalyst, and outputting exhaust from the ventilation system. In some such examples, outputting the exhaust from the cooking appliance ventilation system alternately or additionally comprises directing air into one or more outlets positioned to blow the cooking exhaust from a cooking appliance toward the inlet aperture. In some such examples, the cooking appliance ventilation system alternately or additionally comprises a hood, and wherein outputting the exhaust from the cooking appliance ventilation system alternately or additionally comprises directing air into one or more outlets to form an air curtain that extends downwardly from the hood.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A cooking appliance ventilation system, comprising:
   a ventilation duct comprising an inlet aperture configured to receive cooking exhaust;
   a fan positioned within the ventilation duct and configured to pull the cooking exhaust through the inlet aperture and the ventilation duct;
   an ozone source configured to introduce ozone into the ventilation duct upstream of the fan; and
   one or more ozone mitigation components positioned within the ventilation duct downstream of the ozone source.

2. The cooking appliance ventilation system of claim 1, wherein the one or more ozone mitigation components comprises an ozone reduction catalyst arranged in the ventilation duct.

3. The cooking appliance ventilation system of claim 2, wherein the ozone reduction catalyst comprises a plurality of catalyst units each occupying a portion of a cross-sectional area of the ventilation duct.

4. The cooking appliance ventilation system of claim 3, wherein the plurality of catalyst units are arranged in a catalyst unit holder.

5. The cooking appliance ventilation system of claim 2, wherein the ozone reduction catalyst is located downstream of the fan.

6. The cooking appliance ventilation system of claim 1, wherein the ventilation duct is configured to direct air into one or more outlets positioned to blow cooking exhaust from a cooking appliance toward the inlet aperture.

7. The cooking appliance ventilation system of claim 1, further comprising a hood, wherein the ventilation duct is configured to direct air into one or more outlets that are positioned to form an air curtain that extends downwardly from the hood.

8. The cooking appliance ventilation system of claim 1, further comprising an ozone generator.

9. The cooking appliance ventilation system of claim 8, further comprising a hood and one or more baffles positioned within the hood at the inlet aperture, and further comprising an ozone outlet configured to introduce ozone from the ozone generator into the ventilation duct downstream of the one or more baffles.

10. The cooking appliance ventilation system of claim 1, wherein the cooking appliance ventilation system is integrated with a cooking appliance.

11. The cooking appliance ventilation system of claim 1, wherein the cooking appliance ventilation system is configured to be positioned at least partially over a cooking appliance.

12. A cooking appliance ventilation system, comprising:
    a ventilation duct comprising an inlet aperture configured to receive cooking exhaust;
    a fan positioned within the ventilation duct downstream of the inlet aperture;
    an ozone generator and an ozone outlet configured to introduce ozone into the ventilation duct upstream of the fan; and
    an ozone reduction catalyst located within the ventilation duct, the ozone reduction catalyst comprising a plurality of catalyst units arranged in a catalyst holder, each catalyst unit occupying a portion of a cross-sectional area of the ventilation duct.

13. The cooking appliance ventilation system of claim 12, wherein each catalyst unit has a rectangular block shape.

14. The cooking appliance ventilation system of claim 12, wherein the plurality of catalyst units are arranged in the catalyst holder to form a wall that substantially fills a cross-sectional area of a portion of the ventilation duct.

15. The cooking appliance ventilation system of claim 12, wherein the ventilation duct is configured to direct air into one or more outlets positioned to blow cooking exhaust from a cooking appliance toward the inlet aperture.

16. The cooking appliance ventilation system of claim 12, further comprising a hood, wherein the ventilation duct is configured to direct air into one or more outlets that are positioned to form an air curtain that extends downwardly from the hood.

17. A method of operating a cooking appliance ventilation system, comprising:
    drawing cooking exhaust into a ventilation duct via a fan positioned within the ventilation duct;

introducing ozone into the ventilation duct upstream of the fan to oxidize one or more of grease and particulate matter in the cooking exhaust;

filtering the cooking exhaust;

reducing ozone in the ventilation duct via an ozone reduction catalyst located downstream of the fan; and outputting exhaust from the ventilation duct.

18. The method of claim 17, wherein outputting the exhaust from the cooking appliance ventilation system comprises directing air into one or more outlets positioned to blow the cooking exhaust from a cooking appliance toward an inlet aperture of the ventilation duct.

19. The method of claim 17, wherein the cooking appliance ventilation system further comprising a hood, and wherein outputting the exhaust from the cooking appliance ventilation system comprises directing air into one or more outlets to form an air curtain that extends downwardly from the hood.

* * * * *